United States Patent
Valkirs et al.

(10) Patent No.: US 7,393,647 B2
(45) Date of Patent: *Jul. 1, 2008

(54) **METHODS FOR DETECTING *B. ANTHRACIS* INFECTION**

(75) Inventors: Gunars Edwin Valkirs, Escondido, CA (US); Kenneth Buechler, Rancho Sante Fe, CA (US)

(73) Assignee: Biosite Incorporated, San Diego, CA (US)

( * ) Notice: Subject to any disclaimer, the term of this patent is extended or adjusted under 35 U.S.C. 154(b) by 726 days.

This patent is subject to a terminal disclaimer.

(21) Appl. No.: 10/447,300

(22) Filed: May 27, 2003

(65) Prior Publication Data

US 2008/0124747 A1    May 29, 2008

(51) Int. Cl.
*G01N 33/53* (2006.01)
*C12N 1/00* (2006.01)
*A61K 39/07* (2006.01)
*C12P 21/04* (2006.01)
*C07H 21/04* (2006.01)

(52) U.S. Cl. .................. 435/7.1; 435/4; 435/5; 435/6; 435/7.2; 435/7.21; 435/7.22; 435/7.32; 435/810; 435/7.94; 435/7.95; 435/69.7; 436/501; 436/518; 424/246.1

(58) Field of Classification Search ............... 435/4–7, 435/7.1, 7.2, 7.22, 7.3, 7.32, 7.95, 810, 69.7; 424/246.1; 436/501, 518

See application file for complete search history.

(56) References Cited

U.S. PATENT DOCUMENTS

| 4,391,904 | A | 7/1983 | Litman et al. |
| 5,496,700 | A | 3/1996 | Ligler et al. |
| 6,448,016 | B1 | 9/2002 | Rastogi et al. |
| 6,828,110 | B2 * | 12/2004 | Lee et al. ............. 435/7.1 |

FOREIGN PATENT DOCUMENTS

WO    WO 01/49823 A2    7/2001

OTHER PUBLICATIONS

Connors et al (Clin Diagn Lab Immunol. Jan. 1994; 1(1): 78-82).*
Jobling et al. (Mol. Microbiol. 1991, 5(7): 1755-67.*
Arnon et al FASEB J. Nov. 1992; 6(14): 3265-74).*
Burgess et al., The Journal of Cell Biology, 111:2129-2138, 1990).*
Lazar et al., Molecular and Cellular Biology, 8(3): 1247-1252, 1988).*
Bruno, et al. "In vitro selection of DNA aptamers to anthrax spores with electrochemiluminescence detection"; *Biosensors & Bioelectronics* (1999) pp. 457-464 vol. 14.
Etienne-Toumelin, et al. "Characterization of the *Bacillus anthracis* S-Layer: Cloning and Sequencing of the Structural Gene", *Journal of Bacteriology* (1995) pp. 614-620 vol. 177, No. 3.
Farchaus, et al. "Purification and Characterization of the Major Surface Array Protein from the Avirulent *Bacillus anthracis* Delta Sterne-1", *Journal of Bacteriology* (1995) pp. 2481-2489 vol. 177, No. 9.
Franz, et al. "Clinical Recognition and Management of Patients Exposed to Biological Warfare Agents", *JAMA* (1997) pp. 399-411 vol. 278, No. 5.
Graham, et al. "Enzyme-Linked Lectinosorbent Assay (ELLA) for Detecting *Bacillus anthracis*", *Eur. J. Clin. Microbiol.* (1984) pp. 210-212 vol. 3, No. 3.
Longchamp and Leighton "Molecular recognition specificity of *Bacillus anthracis* spore antibodies", *Journal of Applied Microbiology* (1999) pp. 246-249 vol. 87.
Mesnage, et al. "Molecular characterization of the *Bacillus anthracis* main S-layer component: evidence that it is the major cell-associated antigen", *Molecular Microbiology* (1997) pp. 1147-1155 vol. 23(6).
Mesnage, et al. "The Capsule and S-Layer: Two Independent and Yet Compatible Macromolecular Structures in *Bacillus anthracis*", *Journal of Bacteriology* (1998) pp. 52-58 vol. 180.
Phillips and Martin "Investigation of spore surface antigens in the genus *Bacillus* by the use of polyclonal antibodies in immunofluorescence tests", *Journal of Applied Bacteriology* (1988) pp. 47-55 vol. 64.
Phillips, et al. "Monoclonal antibodies against spore antigens of *Bacillus anthracis*", FEMS Microbiology Immunology (1988) pp. 169-178 vol. 47.
Yu, "Comparative studies of magnetic particle-based solid phase fluorogenic and electrochemiluminescent imunoassay", *Journal of Immunological Methods* (1998) pp. 1-8 vol. 218.

* cited by examiner

*Primary Examiner*—Shanon Foley
*Assistant Examiner*—Padma Baskar
(74) *Attorney, Agent, or Firm*—Wilson Sonsini Goodrich and Rosati, P.C.

(57) ABSTRACT

This invention pertains to methods for detecting *B. anthracis* and antibodies to *B. anthracis*, the causative agent of anthrax, in a subject.

22 Claims, No Drawings

SEQUENCE LISTING

<160> NUMBER OF SEQ ID NOS: 8

<210> SEQ ID NO 1
<211> LENGTH: 785
<212> TYPE: PRT
<213> ORGANISM: Bacillus anthracis
<220> FEATURE:
<223> OTHER INFORMATION: S-layer surface array protein (SAP)

<400> SEQUENCE: 1

```
Ala Gly Lys Thr Phe Pro Asp Val Pro Ala Asp His Trp Gly Ile Asp
 1               5                  10                  15

Ser Ile Asn Tyr Leu Val Glu Lys Gly Ala Val Lys Gly Asn Asp Lys
            20                  25                  30

Gly Met Phe Glu Pro Gly Lys Glu Leu Thr Arg Ala Glu Ala Ala Thr
        35                  40                  45

Met Met Ala Gln Ile Leu Asn Leu Pro Ile Asp Lys Asp Ala Lys Pro
    50                  55                  60

Ser Phe Ala Asp Ser Gln Gly Gln Trp Tyr Thr Pro Phe Ile Ala Ala
65                  70                  75                  80

Val Glu Lys Ala Gly Val Ile Lys Gly Thr Gly Asn Gly Phe Glu Pro
                85                  90                  95

Asn Gly Lys Ile Asp Arg Val Ser Met Ala Ser Leu Leu Val Glu Ala
            100                 105                 110

Tyr Lys Leu Asp Thr Lys Val Asn Gly Thr Pro Ala Thr Lys Phe Lys
        115                 120                 125

Asp Leu Glu Thr Leu Asn Trp Gly Lys Glu Lys Ala Asn Ile Leu Val
    130                 135                 140

Glu Leu Gly Ile Ser Val Gly Thr Gly Asp Gln Trp Glu Pro Lys Lys
145                 150                 155                 160

Thr Val Thr Lys Ala Glu Ala Ala Gln Phe Ile Ala Lys Thr Asp Lys
                165                 170                 175

Gln Phe Gly Thr Glu Ala Ala Lys Val Glu Ser Ala Lys Ala Val Thr
            180                 185                 190

Thr Gln Lys Val Glu Val Lys Phe Ser Lys Ala Val Glu Lys Leu Thr
        195                 200                 205

Lys Glu Asp Ile Lys Val Thr Asn Lys Ala Asn Asn Asp Lys Val Leu
    210                 215                 220

Val Lys Glu Val Thr Leu Ser Glu Asp Lys Arg Ser Ala Thr Val Glu
225                 230                 235                 240

Leu Tyr Ser Asn Leu Ala Ala Lys Gln Thr Tyr Thr Val Asp Val Asn
                245                 250                 255

Lys Val Gly Lys Thr Glu Val Ala Val Gly Ser Leu Glu Ala Lys Thr
            260                 265                 270

Ile Glu Met Ala Asp Gln Thr Val Val Ala Asp Glu Pro Thr Ala Leu
        275                 280                 285

Gln Phe Thr Val Lys Asp Glu Asn Gly Thr Glu Val Val Ser Pro Glu
    290                 295                 300

Gly Ile Glu Phe Val Thr Pro Ala Ala Glu Lys Ile Asn Ala Lys Gly
305                 310                 315                 320

Glu Ile Thr Leu Ala Lys Gly Thr Ser Thr Val Lys Ala Val Tyr
                325                 330                 335

Lys Lys Asp Gly Lys Val Val Ala Glu Ser Lys Glu Val Lys Val Ser
            340                 345                 350
```

```
Ala Glu Gly Ala Ala Val Ala Ser Ile Ser Asn Trp Thr Val Ala Glu
            355                 360                 365

Gln Asn Lys Ala Asp Phe Thr Ser Lys Asp Phe Lys Gln Asn Asn Lys
        370                 375                 380

Val Tyr Glu Gly Asp Asn Ala Tyr Val Gln Val Glu Leu Lys Asp Gln
385                     390                 395                 400

Phe Asn Ala Val Thr Thr Gly Lys Val Glu Tyr Glu Ser Leu Asn Thr
                405                 410                 415

Glu Val Ala Val Val Asp Lys Ala Thr Gly Lys Val Thr Val Leu Ser
            420                 425                 430

Ala Gly Lys Ala Pro Val Lys Val Thr Val Lys Asp Ser Lys Gly Lys
        435                 440                 445

Ala Leu Val Ser His Thr Val Glu Ile Glu Ala Phe Ala Gln Lys Ala
    450                 455                 460

Met Lys Asp Ile Lys Leu Glu Lys Thr Asn Val Ala Leu Ser Thr Lys
465                 470                 475                 480

Asp Val Thr Asp Leu Lys Val Lys Ala Pro Val Leu Asp Gln Tyr Gly
                485                 490                 495

Lys Glu Phe Thr Ala Pro Val Thr Val Lys Val Leu Asp Lys Asp Gly
            500                 505                 510

Lys Glu Leu Lys Glu Gln Lys Leu Glu Ala Lys Tyr Val Asn Arg Glu
        515                 520                 525

Leu Val Leu Asn Ala Ala Gly Gln Glu Ala Gly Asn Tyr Thr Val Val
    530                 535                 540

Leu Thr Ala Lys Ser Gly Glu Lys Glu Ala Lys Ala Thr Leu Ala Leu
545                 550                 555                 560

Glu Leu Lys Ala Pro Gly Ala Phe Ser Lys Phe Glu Val Arg Gly Leu
                565                 570                 575

Asp Thr Glu Leu Asp Lys Tyr Val Thr Glu Glu Asn Gln Lys Asn Ala
            580                 585                 590

Met Thr Val Ser Val Leu Pro Val Asp Ala Asn Gly Leu Val Leu Lys
        595                 600                 605

Gly Ala Glu Ala Ala Glu Leu Lys Val Thr Thr Thr Asn Lys Glu Gly
    610                 615                 620

Lys Glu Val Asp Ala Thr Asp Ala Gln Val Thr Val Gln Asn Asn Ser
625                 630                 635                 640

Val Ile Thr Val Gly Gln Gly Ala Lys Ala Gly Glu Thr Tyr Lys Val
                645                 650                 655

Thr Val Val Leu Asp Gly Lys Leu Ile Thr Thr His Ser Phe Lys Val
            660                 665                 670

Val Asp Thr Ala Pro Thr Ala Lys Gly Leu Ala Val Glu Phe Thr Ser
        675                 680                 685

Thr Ser Leu Lys Glu Val Ala Pro Asn Ala Asp Leu Lys Ala Ala Leu
    690                 695                 700

Leu Asn Ile Leu Ser Val Asp Gly Val Pro Ala Thr Thr Ala Lys Ala
705                 710                 715                 720

Thr Ala Ser Asn Val Glu Phe Val Ser Ala Asp Thr Asn Val Val Ala
                725                 730                 735

Glu Asn Gly Thr Val Gly Ala Lys Gly Ala Thr Ser Ile Tyr Val Lys
            740                 745                 750

Asn Leu Thr Val Val Lys Asp Gly Lys Glu Gln Lys Val Glu Phe Asp
        755                 760                 765
```

-continued

Lys Ala Val Gln Val Ala Val Ser Ile Lys Glu Ala Lys Pro Ala Thr
        770                 775                 780
Lys
785

<210> SEQ ID NO 2
<211> LENGTH: 2370
<212> TYPE: DNA
<213> ORGANISM: Bacillus anthracis
<220> FEATURE:
<223> OTHER INFORMATION: S-layer surface array protein (SAP) cDNA

<400> SEQUENCE: 2

| | | | | | |
|---|---|---|---|---|---|
| aaaacattcc | cagacgttcc | tgctgatcac | tggggaattg | attccattaa | ctacttagta | 60 |
| gaaaaaggcg | cagttaaagg | taacgacaaa | ggaatgttcg | agcctggaaa | agaattaact | 120 |
| cgtgcagaag | cagctacaat | gatggctcaa | atcttaaact | taccaatcga | taaagatgct | 180 |
| aaaccatctt | tcgctgactc | tcaaggccaa | tggtacactc | cattcatcgc | agctgtagaa | 240 |
| aaagctggcg | ttattaaagg | tacaggaaac | ggctttgagc | caaacggaaa | aatcgaccgc | 300 |
| gtttctatgg | catctcttct | tgtagaagct | tacaaattag | atactaaagt | aaacggtact | 360 |
| ccagcaacta | aattcaaaga | tttagaaaca | ttaaactggg | gtaaagaaaa | agctaacatc | 420 |
| ttagttgaat | taggaatctc | tgttggtact | ggtgatcaat | gggagcctaa | gaaaactgta | 480 |
| actaaagcag | aagctgctca | attcattgct | aagactgaca | agcagttcgg | tacagaagca | 540 |
| gcaaagttg | aatctgcaaa | agctgttaca | actcaaaaag | tagaagttaa | attcagcaaa | 600 |
| gctgttgaaa | aattaactaa | agaagatatc | aaagtaacta | acaaagctaa | caacgataaa | 660 |
| gtactagtta | agaggtaac | tttatcagaa | gataaaaagat | ctgctacagt | tgaattatat | 720 |
| agtaacttag | cagctaaaca | aacttacact | gtagatgtaa | acaaagttgg | taaaacagaa | 780 |
| gtagctgtag | gttctttaga | agcaaaaaca | atcgaaatgg | ctgaccaaac | agttgtagct | 840 |
| gatgagccaa | cagcattaca | attcacagtt | aaagatgaaa | acggtactga | agttgtttca | 900 |
| ccagagggta | ttgaatttgt | aacgccagct | gcagaaaaaa | ttaatgcaaa | aggtgaaatc | 960 |
| actttagcaa | aaggtacttc | aactactgta | aaagctgttt | ataaaaaaga | cggtaaagta | 1020 |
| gtagctgaaa | gtaaagaagt | aaaagtttct | gctgaaggtg | ctgcagtagc | ttcaatctct | 1080 |
| aactggacag | ttgcagaaca | aaataaagct | gactttactt | ctaaagattt | caaacaaaac | 1140 |
| aataaagttt | acgaaggcga | caacgcttac | gttcaagtag | aattgaaaga | tcaatttaac | 1200 |
| gcagtaacaa | ctggaaaagt | tgaatatgag | tcgttaaaca | cagaagttgc | tgtagtagat | 1260 |
| aaagctactg | gtaaagtaac | tgtattatct | gcaggaaaag | caccagtaaa | agtaactgta | 1320 |
| aaagattcaa | aaggtaaagc | acttgtttca | cacacagttg | aaattgaagc | tttcgctcaa | 1380 |
| aaagcaatga | agacattaa | attagaaaaa | actaacgtag | cgctttctac | aaaagatgta | 1440 |
| acagatttaa | agtaaaagc | tccagtacta | gatcaatacg | gtaaagagtt | tacagctcct | 1500 |
| gtaacagtga | agtacttga | taaagatggt | aaagaattaa | agaacaaaa | attagaagct | 1560 |
| aaatatgtga | acagagaatt | agttctgaat | gcagcaggtc | aagaagctgg | taattataca | 1620 |
| gttgtattaa | ctgcaaaatc | tggtgaaaaa | gaagcaaaag | ctacattagc | tctagaatta | 1680 |
| aaagctccag | gtgcattctc | taaatttgaa | gttcgtggtt | tagacacaga | attagataaa | 1740 |
| tatgttactg | aggaaaacca | aaagaatgca | atgactgttt | cagttcttcc | tgtagatgca | 1800 |
| aatgattag | tattaaaagg | tgcagaagca | gctgaactaa | agtaacaac | aacaaacaaa | 1860 |
| gaaggtaaag | aagtagacgc | aactgatgca | caagttactg | tacaaaataa | cagtgtaatt | 1920 |

-continued

```
actgttggtc aaggtgcaaa agctggtgag acttataaag taacagttgt actagatggt    1980
aaattaatca caactcattc attcaaagtt gttgatacag caccaactgc taaaggatta    2040
gcagtagaat ttacaagcac atctcttaaa gaagtagctc caaatgctga tttaaaagct    2100
gcacttttaa atatcttatc tgttgatggt gtacctgcga ctacagcaaa agcaacagct    2160
tctaatgtag aatttgtttc tgctgacaca aatgttgtag ctgaaaatgg tacagttggt    2220
gcaaaaggtg caacatctat ctatgtgaaa aacctgacag ttgtaaaaga tggaaaagag    2280
caaaaagtag aatttgataa agctgtacaa gttgcagttt ctattaaaga agcaaaacct    2340
gcaacaaaac atcaccatca ccatcactaa                                     2370
```

<210> SEQ ID NO 3
<211> LENGTH: 44
<212> TYPE: DNA
<213> ORGANISM: Artificial Sequence
<220> FEATURE:
<223> OTHER INFORMATION: Description of Artificial Sequence:5' PCR
      primer

<400> SEQUENCE: 3

```
tcgctgccca accagccatg gccgcaggta aacattccc agac                        44
```

<210> SEQ ID NO 4
<211> LENGTH: 89
<212> TYPE: DNA
<213> ORGANISM: Artificial Sequence
<220> FEATURE:
<223> OTHER INFORMATION: Description of Artificial Sequence:3' PCR
      primer

<400> SEQUENCE: 4

```
gtgataaact accgcattaa agcttatcga tgataagctg tcaattagtg atggtgatgg     60
tgatgttttg ttgcaggttt tgcttctttt                                      89
```

<210> SEQ ID NO 5
<211> LENGTH: 200
<212> TYPE: PRT
<213> ORGANISM: Artificial Sequence
<220> FEATURE:
<223> OTHER INFORMATION: Description of Artificial Sequence:poly-Gly
      flexible linker
<220> FEATURE:
<221> NAME/KEY: MOD_RES
<222> LOCATION: (6)..(200)
<223> OTHER INFORMATION: Gly residues from position 6 to 200 may be
      present or absent

<400> SEQUENCE: 5

```
Gly Gly Gly Gly Gly Gly Gly Gly Gly Gly Gly Gly Gly Gly Gly
 1               5                  10                  15

Gly Gly Gly Gly Gly Gly Gly Gly Gly Gly Gly Gly Gly Gly Gly
            20                  25                  30

Gly Gly Gly Gly Gly Gly Gly Gly Gly Gly Gly Gly Gly Gly Gly
        35                  40                  45

Gly Gly Gly Gly Gly Gly Gly Gly Gly Gly Gly Gly Gly Gly Gly
    50                  55                  60

Gly Gly Gly Gly Gly Gly Gly Gly Gly Gly Gly Gly Gly Gly Gly
 65                  70                  75                  80

Gly Gly Gly Gly Gly Gly Gly Gly Gly Gly Gly Gly Gly Gly Gly
            85                  90                  95
```

```
Gly Gly Gly Gly Gly Gly Gly Gly Gly Gly Gly Gly Gly Gly Gly
            100                 105                 110

Gly Gly Gly Gly Gly Gly Gly Gly Gly Gly Gly Gly Gly Gly Gly
        115                 120                 125

Gly Gly Gly Gly Gly Gly Gly Gly Gly Gly Gly Gly Gly Gly Gly
    130                 135                 140

Gly Gly Gly Gly Gly Gly Gly Gly Gly Gly Gly Gly Gly Gly Gly
145                 150                 155                 160

Gly Gly Gly Gly Gly Gly Gly Gly Gly Gly Gly Gly Gly Gly Gly
                165                 170                 175

Gly Gly Gly Gly Gly Gly Gly Gly Gly Gly Gly Gly Gly Gly Gly
            180                 185                 190

Gly Gly Gly Gly Gly Gly Gly Gly
        195                 200

<210> SEQ ID NO 6
<211> LENGTH: 201
<212> TYPE: PRT
<213> ORGANISM: Artificial Sequence
<220> FEATURE:
<223> OTHER INFORMATION: Description of Artificial Sequence:flexible
      linker
<220> FEATURE:
<221> NAME/KEY: MOD_RES
<222> LOCATION: (1)..(97)
<223> OTHER INFORMATION: Gly residues from position 1 to 97 may be
      present or absent
<220> FEATURE:
<221> NAME/KEY: MOD_RES
<222> LOCATION: (105)..(201)
<223> OTHER INFORMATION: Gly residues from position 105 to 201 may be
      present or absent

<400> SEQUENCE: 6

Gly Gly Gly Gly Gly Gly Gly Gly Gly Gly Gly Gly Gly Gly Gly
  1               5                  10                  15

Gly Gly Gly Gly Gly Gly Gly Gly Gly Gly Gly Gly Gly Gly Gly
             20                  25                  30

Gly Gly Gly Gly Gly Gly Gly Gly Gly Gly Gly Gly Gly Gly Gly
         35                  40                  45

Gly Gly Gly Gly Gly Gly Gly Gly Gly Gly Gly Gly Gly Gly Gly
     50                  55                  60

Gly Gly Gly Gly Gly Gly Gly Gly Gly Gly Gly Gly Gly Gly Gly
 65                  70                  75                  80

Gly Gly Gly Gly Gly Gly Gly Gly Gly Gly Gly Gly Gly Gly Gly
                 85                  90                  95

Gly Gly Gly Gly Pro Gly Gly Gly Gly Gly Gly Gly Gly Gly Gly
            100                 105                 110

Gly Gly Gly Gly Gly Gly Gly Gly Gly Gly Gly Gly Gly Gly Gly
        115                 120                 125

Gly Gly Gly Gly Gly Gly Gly Gly Gly Gly Gly Gly Gly Gly Gly
    130                 135                 140

Gly Gly Gly Gly Gly Gly Gly Gly Gly Gly Gly Gly Gly Gly Gly
145                 150                 155                 160

Gly Gly Gly Gly Gly Gly Gly Gly Gly Gly Gly Gly Gly Gly Gly
                165                 170                 175

Gly Gly Gly Gly Gly Gly Gly Gly Gly Gly Gly Gly Gly Gly Gly
            180                 185                 190

Gly Gly Gly Gly Gly Gly Gly Gly Gly
```

-continued

```
        195                 200

<210> SEQ ID NO 7
<211> LENGTH: 6
<212> TYPE: PRT
<213> ORGANISM: Artificial Sequence
<220> FEATURE:
<223> OTHER INFORMATION: Description of Artificial Sequence:
      hexahistidine tag

<400> SEQUENCE: 7

His His His His His His
  1               5

<210> SEQ ID NO 8
<211> LENGTH: 12
<212> TYPE: DNA
<213> ORGANISM: Artificial Sequence
<220> FEATURE:
<223> OTHER INFORMATION: Description of Artificial Sequence:oligo dT-12

<400> SEQUENCE: 8
tttttttttt tt                                                          12
```

METHODS FOR DETECTING B. ANTHRACIS INFECTION

FIELD OF THE INVENTION

This invention pertains to methods for detecting *B. anthracis* and antibodies to *B. anthracis*, the causative agent of anthrax, in a subject.

BACKGROUND OF THE INVENTION

Anthrax spores were first produced as weapons in the 1950s. Several countries including the former Soviet Union, the United States and Iraq are known to have produced anthrax weapons. Anthrax is a particularly fearsome biological warfare agent, not only because of its deadliness, but also because anthrax weapons are relatively easy to produce and deliver. Production of anthrax spores requires little more than basic laboratory equipment and growth media. Anthrax weapons may be comprised of an anthrax source and an industrial sprayer that can produce aerosol particles of the appropriate size for victims to inhale. Such sprayers, for instance, can be mounted on low flying airplanes or other vehicles and used to spread anthrax over a wide area. Because of the ease and relatively small expense involved in producing and delivering anthrax weapons, such weapons are potentially highly attractive weapons of mass destruction for terrorist groups. Thus, in addition to potential organized military conflicts that may give rise to the use of such weapons, terrorist organizations are a potential threat for the use of such weapons in airports, office buildings and other centers of human activity.

Anthrax is caused by *B. anthracis*, a gram-positive, sporulating *bacillus*. *B. anthracis* is a soil bacterium and is distributed worldwide. The organism exists in the infected host as a vegetative *bacillus* and in the environment as a spore. The anthrax spore is typically the infective form of the bacterial life cycle. Anthrax spores can survive adverse environmental conditions and can remain viable for decades. Animals such as cattle, sheep, goats and horses can contract the spores while grazing. Humans can contract anthrax from inoculation of minor skin lesions with spores from infected animals, their hides, wool or other products, such as infected meat (Franz et al. (1997) *J. Am. Med. Assoc.* 278(5): 399-411).

The typical mode of entry of the anthrax spore into the body, inhalation, results in an illness known as woolsorter's disease. After deposit in the lower respiratory tract, spores are phagocytized by tissue macrophages and transported to hilar and mediastinal lymph nodes. The spores germinate into vegetative bacilli, producing a necrotizing hemorrhagic mediastinitis (Franz et al., supra). Symptoms include fever, malaise and fatigue, which can easily be confused with the flu. The disease may progress to an abrupt onset of severe respiratory distress with dyspnea, stridor, diaphoresis and cyanosis. Death usually follows within 24 to 36 hours.

Cutaneous anthrax infection occurs following external contact with anthrax. In cutaneous anthrax infection, symptoms include a skin infection that is distinguished by a raised itchy bump that resembles an insect bite in the first days and develops into a vesicle and then ulcer with a characteristic black necrotic area in the center. 20% of untreated cases of cutaneous infection result in death.

Gastrointestinal anthrax infection follows consumption of contaminated meat. Symptoms include nausea, loss of appetite, vomiting, fever, abdominal pain, vomiting of blood and severe diarrhea. Death results in 25%-60% of cases.

Because the effects of exposure to anthrax are not immediate, and because the initial symptoms are easily confused with the flu, there is a need for a fast method to detect *B. anthracis* in a subject. This need is enhanced by the increasing number of anthrax threats that are called into governmental authorities each year and the recent transport of anthrax through the United States Postal System. A fast method for determining whether a subject has been infected with anthrax is, therefore, essential.

Anthrax spores have S-layers, as do spores of many other archea and bacteria. Most S-layers are comprised of repeats of a single protein (Etienne-Toumelin et al., *J. Bacteriol.* 177:614-20 (1995)). The S-layer of *B. anthracis*, however, is comprised of at least two proteins: EA1 (Mesnage et al., *Molec. Microbiol.* 23:1147-55 (1997)) and surface array protein (SAP) (see Etienne-Toumelin, et al., supra). Fully virulent *B. anthracis* isolates are encapsulated by a capsule that encompasses the S-layer of the bacteria and prevents access of antibodies to both EA1 and SAP (Mesnage et al., *J. Bacteriol.* 180:52-58 (1998)). Amino acids 180 to 700 of SEQ ID NO:1 are specific for SAP.

A fast and efficient method is needed to detect infection of animals, and especially humans, by anthrax. The present invention addresses this and other problems.

SUMMARY OF THE INVENTION

The present invention provides novel methods of detecting antibodies and antigens to *B. anthracis*. In one embodiment of the invention, a method for the detection of an anti-*B. anthracis* antibody present in a biological sample comprises two steps. The first step comprises contacting a biological sample from an animal with an affinity agent comprising an epitope recognized by an antibody that specifically binds to SEQ ID NO:1, wherein the affinity agent forms a complex with the anti-*B. anthracis* antibody if the anti-*B. anthracis* antibody is present in the sample. The second step comprises detecting the presence or absence of the complex, wherein the presence of the complex indicates the presence of antibodies to *B. anthracis* in the sample.

In one embodiment of the invention, the complex is detected prior to clinical manifestation of anthrax in the animal.

In one embodiment of the invention, the affinity agent comprises a polypeptide at least 80% identical to SEQ ID NO:1 or a fragment of SEQ ID NO:1 at least 10 amino acids long. In another embodiment, the affinity agent comprises SEQ ID NO:1. In yet another embodiment, the affinity agent comprises a polypeptide at least 80% identical to amino acids 180 to 700 of SEQ ID NO:1 or a fragment of amino acids 180 to 700 of SEQ ID NO:1 at least 10 amino acids long.

In one aspect of the invention, the animal contacted is a human. In another aspect of the invention, the biological sample taken from the animal is bodily fluid. In one aspect of the invention, the bodily fluid is blood which may be further processed to serum or plasma.

In one embodiment of the invention, the affinity agent is immobilized on a solid support. In one aspect of the invention, the solid support is a microtiter dish. In another embodiment, the method for the detection of an anti *B. anthracis* antibody further comprises contacting the complex with an antibody that binds to the complex. In one aspect of the invention, the antibody is labeled. In another aspect, the label is selected from the group consisting of enzymes, radioisotopes, fluorescent compounds, colloidal metals, chemiluminescent compounds, phosphorescent compounds and bioluminescent compounds. In yet another aspect of the invention, the antibody specifically binds to a human antibody.

In one embodiment of the invention, the anti-*B. anthracis* antibody detected is an IgG isotype. In another embodiment, the anti-*B. anthracis* antibody detected is an IgM isotype. In yet another embodiment of the invention, the anti-*B. anthracis* antibodies detected comprise IgG and IgM isotypes.

In one embodiment of the invention, the method further comprises the steps of contacting the biological sample with a capture reagent, wherein the capture reagent forms a complex with a *B. anthracis* surface array protein if the surface array protein is present in the sample, and detecting the presence or absence of the complex.

In one aspect of the invention the biological sample is blood or plasma.

In one embodiment of the invention, the surface array protein comprises a polypeptide having an amino acid sequence at least 80% identical to SEQ ID NO:1 or a fragment of SEQ ID NO:1 at least 10 amino acids long. In another embodiment, the polypeptide comprises SEQ ID NO:1. In yet another embodiment, the surface array protein comprises a polypeptide having an amino acid sequence at least 80% identical to amino acids 180 to 700 of SEQ ID NO:1 or a fragment of amino acids 180 to 700 of SEQ ID NO:1 at least 10 amino acids long.

In one embodiment of the invention, the capture reagent comprises an antibody that binds to SEQ ID NO:1. In one aspect of the invention, the capture reagent is a recombinant antibody. In another aspect, the capture reagent is a recombinant polyclonal antibody. In yet another aspect, the capture reagent is a monoclonal antibody.

In one embodiment, the capture reagent is immobilized on a solid support. In one embodiment of the invention, the capture reagent is immobilized on the same solid support as the affinity agent. In another embodiment, the solid support is a microtiter dish.

The present invention further provides a method for detecting the surface array protein comprising contacting the surface array protein with a detection reagent that can bind to the surface array protein. In one aspect of the invention, the detection reagent is an antibody that binds to the complex. In one embodiment, the detection reagent is labeled.

The invention also provides a kit for the detection of an anti-*B. anthracis* antibody in a biological sample. In some embodiments, the kit comprises an affinity agent immobilized on a solid support. In some embodiments, the affinity agent comprises an epitope recognized by an antibody that specifically binds to SEQ ID NO:1, wherein the affinity agent forms a complex with the anti-*B. anthracis* antibody if the anti-*B. anthracis* antibody is contacted to the affinity agent. In one embodiment of the invention, the affinity agent comprises SEQ ID NO:1 or a fragment of SEQ ID NO:1 at least 10 amino acids long. In yet another embodiment, the affinity agent comprises a polypeptide at least 80% identical to amino acids 180 to 700 of SEQ ID NO:1 or a fragment of amino acids 180 to 700 of SEQ ID NO:1 at least 10 amino acids long.

In one aspect of the invention, the solid support provided in the kit comprises a microtiter plate and the affinity agent is present in the wells of the microtiter plate.

In one embodiment of the invention, the kit comprises a detection reagent. In one aspect, the detection reagent provided in the kit comprises an antibody that binds to the complex. In another aspect, the antibody is labeled. In yet anther aspect, the label is selected from the group consisting of enzymes, radioisotopes, fluorescent compounds, colloidal metals, chemiluminescent compounds, phosphorescent compounds and bioluminescent compounds.

In one embodiment of the invention, the antibody provided in the kit specifically binds to a human antibody. In one aspect of the invention, the human antibody detected comprises IgG and IgM isotypes.

In another embodiment of the invention, the kit further comprises a capture reagent immobilized on a solid support, wherein the capture reagent forms a complex with a *B. anthracis* surface array protein if the surface array protein is present in the sample. In one aspect, the capture reagent and affinity agent are immobilized on the same solid support. In another aspect, the capture reagent is immobilized on a microtiter dish.

In one embodiment of the invention, the capture reagent provided in the kit is an antibody. In one aspect, the capture reagent is a recombinant polyclonal antibody. In yet another aspect, the capture reagent is a monoclonal antibody.

In another embodiment, the kit further comprises a positive control that comprises a polypeptide that comprises an antigenic determinant of a *B. anthracis* surface array protein. In one aspect of the invention, the antigenic determinant comprises an amino acid sequence of SEQ ID NO:1 or a fragment of SEQ ID NO:1 at least 10 amino acids long. In yet another aspect, the antigenic determinant comprises a polypeptide at least 80% identical to amino acids 180 to 700 of SEQ ID NO:1 or a fragment of amino acids 180 to 700 of SEQ ID NO:1 at least 10 amino acids long.

In one embodiment of the invention, the kit comprises a detection reagent. In one aspect, the detection reagent comprises an antibody that binds to the complex. In another aspect of the invention, the antibody is labeled.

DETAILED DESCRIPTION

I. Introduction

The present invention provides methods for detecting *B. anthracis* infection in an animal. More specifically, this invention provides methods for detecting antibodies that specifically bind to a *B. anthracis* surface array protein (SAP) in an animal. *B. anthracis* SAP is an antigen or antigenic determinant that is specific for *B. anthracis*. Therefore, detection of antibodies in a biological sample that specifically bind to SAP indicate that an animal has been exposed to *B. anthracis* and may be infected with anthrax.

The present invention also provides methods for detecting the *B. anthracis* surface array protein in an animal. The *B. anthracis* SAP polypeptide in the animal can be an antigen or antigenic determinant that is specific for *B. anthracis*. Detecting *B. anthracis* surface array protein in an animal also indicates that an animal has been exposed to *B. anthracis* and may be infected with anthrax.

II. Definitions

The phrase "capture reagent" refers to a molecule that specifically binds to a surface array protein of *B. anthracis* or a portion thereof. Capture reagents include naturally and non-naturally-occurring molecules that can specifically bind a target molecule. For instance, antibodies, as well as peptides that specifically bind a target molecule and are developed using phage display or other combinatorial system are encompassed by this definition.

The phrase "affinity agent" refers to a molecule that specifically binds to antibodies specific for a *B. anthracis* surface array protein. Affinity agents include naturally- and non-naturally-occurring molecules that can specifically bind to such antibodies. Affinity agents, include, any type of molecule recognized by antibodies specific for SAP, including, e.g., polypeptides.

The phrase "surface array polypeptide" or "SAP polypeptide" refers to a polypeptide associated with the S-layer of *B. anthracis*. SAP polypeptides are typically one of the most abundant, endogenous polypeptides in *B. anthracis*. See, e.g., Etienne-Toumelin et al., *J. Bacteriol.* 177:614-620 (1995). Exemplary SAP polypeptides include, e.g., SEQ ID NO:1.

A "biological sample" as used herein is a sample of biological tissue or fluid that contains an analyte (such as, antibodies or antigens of interest). These samples can be tested by the methods described herein and include human and animal body fluids such as whole blood, serum, plasma, cerebrospinal fluid, urine, lymph fluids, and various external secretions of the respiratory, intestinal and genitourinary tracts, tears, saliva, milk, white blood cells, myelomas, and the like; and biological fluids such as cell culture supernatants; fixed tissue specimens; and fixed cell specimens. Biological samples may also include sections of tissues such as biopsy and autopsy samples or frozen sections taken for histologic purposes. A biological sample is typically obtained from a eukaryotic organism, most preferably a mammal such as a primate, e.g., human or chimpanzee; cow; dog; cat; a rodent, e.g., guinea pig, rat, mouse; rabbit; or other mammal; or a bird; reptile; or fish. A biological sample can be from a laboratory source or from a non-laboratory source that is either known or not known to contain *B. anthracis* or antibodies to *B. anthracis*.

The term "analyte" refers to the substance to be detected that may be present in the sample. The analyte can be any substance for which there exists a naturally occurring specific binding member (such as an antibody or antigen), or for which a specific binding member can be prepared. Thus, an analyte is a substance that can bind to one or more specific binding members in an assay. "Analyte" also includes any antigenic substances, haptens, antibodies, and combinations thereof. The analyte can include a protein, a peptide, an amino acid, a nucleotide target, and the like.

The phrases "specifically binds to" or "specifically immunoreactive with", when referring to an antibody or other binding moiety, such as the capture reagents or affinity agents described herein, refers to a binding reaction which is determinative of the presence of a target analyte in the presence of a heterogeneous population of proteins and other biologics. Thus, under designated assay conditions, the specified binding moieties, e.g., capture reagents or affinity agents, bind preferentially to a particular target analyte and do not bind in a significant amount to other components present in a sample. Specific binding to a target analyte under such conditions may require a binding moiety that is selected for its specificity for a particular target analyte. Such a binding moiety might include a particular epitope specifically immunoreactive with a particular antibody. Typically a specific or selective reaction will be at least twice background signal or noise and more typically more than 10 to 100 times background.

The term "epitope" means an antigenic determinant that is capable of specific binding to an antibody. Epitopes usually consist of chemically active surface groupings of molecules such as amino acids or sugar side chains and usually have specific three dimensional structural characteristics, as well as specific charge characteristics. Conformational and non-conformational epitopes are distinguished in that the binding to the former but not the latter is lost in the presence of denaturing solvents. Epitopes can include non-contiguous amino acids, as well as contiguous amino acids.

"Antibody" refers to a polypeptide substantially encoded by an immunoglobulin gene or immunoglobulin genes, or fragments thereof which specifically bind and recognize an analyte (antigen or antibody). The recognized immunoglobulin genes include the kappa, lambda, alpha, gamma, delta, epsilon and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist, e.g., as intact immunoglobulins or as a number of well characterized fragments produced by digestion with various peptidases. Thus, for example, pepsin digests an antibody below the disulfide linkages in the hinge region to produce $F(ab)'_2$, a dimer of Fab which itself is a light chain joined to $V_H$-$C_H1$ by a disulfide bond. The $F(ab)'_2$ may be reduced under mild conditions to break the disulfide linkage in the hinge region, thereby converting the $F(ab)'_2$ dimer into an Fab' monomer. The Fab' monomer is essentially a Fab with part of the hinge region (see, Paul (Ed.) *Fundamental Immunology*, Third Edition, Raven Press, NY (1993)). While various antibody fragments are defined in terms of the digestion of an intact antibody, one of skill will appreciate that such fragments may be synthesized de novo either chemically or by utilizing recombinant DNA methodology. Thus, the term antibody, as used herein, also includes antibody fragments either produced by the modification of whole antibodies or those synthesized de novo using recombinant DNA methodologies (e.g., single chain Fv).

The terms "peptidomimetic" and "mimetic" refer to a synthetic chemical compound that has substantially the same structural and functional characteristics of a polypeptide, e.g., a SAP polypeptide. Peptide analogs are commonly used in the pharmaceutical industry as non-peptide drugs with properties analogous to those of the template peptide. These types of non-peptide compound are termed "peptide mimetics" or "peptidomimetics" (Fauchere, *J. Adv. Drug Res.* 15:29 (1986); Veber and Freidinger *TINS* p. 392 (1985); and Evans et al. *J. Med. Chem.* 30:1229 (1987), which are incorporated herein by reference). Peptide mimetics that are structurally similar to therapeutically useful peptides may be used to produce an equivalent or enhanced therapeutic or prophylactic effect. Generally, peptidomimetics are structurally similar to a paradigm polypeptide (i.e., a polypeptide that has a biological or pharmacological activity), such as SAP polypeptide, but have one or more peptide linkages optionally replaced by a linkage selected from the group consisting of, e.g., —CH2NH—, —CH2S—, —CH2—CH2—, —CH═CH— (cis and trans), —COCH2—, —CH(OH)CH2—, and —CH2SO—. The mimetic can be either entirely composed of synthetic, non-natural analogues of amino acids, or, is a chimeric molecule of partly natural peptide amino acids and partly non-natural analogs of amino acids. The mimetic can also incorporate any amount of natural amino acid conservative substitutions as long as such substitutions also do not substantially alter the mimetic's structure and/or activity. For example, a mimetic composition is within the scope of the invention if it is capable of carrying out the binding or antigenic activities of SAP.

The term "gene" means the segment of DNA involved in producing a polypeptide chain; it includes regions preceding and following the coding region (leader and trailer) as well as intervening sequences (introns) between individual coding segments (exons).

The term "isolated," when applied to a nucleic acid or protein, denotes that the nucleic acid or protein is essentially free of other cellular components with which it is associated in the natural state. It is preferably in a homogeneous state although it can be in either a dry or aqueous solution. Purity and homogeneity are typically determined using analytical chemistry techniques such as polyacrylamide gel electrophoresis or high performance liquid chromatography. A protein that is the predominant species present in a preparation is substantially purified. In particular, an isolated gene is separated from open reading frames that flank the gene and encode a protein other than the gene of interest. The term "purified" denotes that a nucleic acid or protein gives rise to essentially one band in an electrophoretic gel. Particularly, it means that the nucleic acid or protein is at least 85% pure, more preferably at least 95% pure, and most preferably at least 99% pure.

The term "nucleic acid" or "polynucleotide" refers to deoxyribonucleotides or ribonucleotides and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); and Cassol et al. (1992); Rossolini et al., *Mol. Cell. Probes* 8:91-98 (1994)). The term nucleic acid is used interchangeably with gene, cDNA, and mRNA encoded by a gene.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers. As used herein, the terms encompass amino acid chains of any length, including full-length proteins (i.e., antigens), wherein the amino acid residues are linked by covalent peptide bonds.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. "Amino acid mimetics" refers to chemical compounds that have a structure that is different from the general chemical structure of an amino acid, but that functions in a manner similar to a naturally occurring amino acid.

Amino acids may be referred to herein by either the commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, "conservatively modified variants" refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein that encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another:

1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)

(see, e.g., Creighton, *Proteins* (1984)).

"Percentage of sequence identity" is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The terms "identical" or percent "identity," in the context of two or more nucleic acids or polypeptide sequences, refer to two or more sequences or subsequences that are the same or have a specified percentage of amino acid residues or nucleotides that are the same (i.e., 60% identity, optionally 65%, 70%, 75%, 80%, 85%, 90%, or 95% identity over a specified region), when compared and aligned for maximum correspondence over a comparison window, or designated region as measured using one of the following sequence comparison algorithms or by manual alignment and visual inspection. Such sequences are then said to be "substantially identical." This definition also refers to the complement of a test sequence. Optionally, the identity exists over a region that is at least about 50 nucleotides in length, or more preferably over a region that is 100 to 500 or 1000 or more nucleotides in length.

The term "similarity," or percent "similarity," in the context of two or more polypeptide sequences, refer to two or more sequences or subsequences that have a specified percentage of amino acid residues that are either the same or similar as defined in the 8 conservative amino acid substitutions defined above (i.e., 60%, optionally 65%, 70%, 75%, 80%, 85%, 90%, or 95% similar over a specified region), when compared and aligned for maximum correspondence over a comparison window, or designated region as measured using one of the following sequence comparison algorithms or by manual alignment and visual inspection. Such sequences are then said to be "substantially similar." Optionally, this identity exists over a region that is at least about 50 amino acids in length, or more preferably over a region that is at least about 100 to 500 or 1000 or more amino acids in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith and Waterman (1970) *Adv. Appl. Math.* 2:482c, by the homology alignment algorithm of Needleman and Wunsch (1970) *J. Mol. Biol.* 48:443, by the search for similarity method of Pearson and Lipman (1988) *Proc. Nat.'l Acad. Sci. USA* 85:2444, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Ausubel et al., *Current Protocols in Molecular Biology* (1995 supplement)).

One example of a useful algorithm is PILEUP. PILEUP creates a multiple sequence alignment from a group of related sequences using progressive, pairwise alignments to show relationship and percent sequence identity. It also plots a tree or dendogram showing the clustering relationships used to create the alignment. PILEUP uses a simplification of the progressive alignment method of Feng and Doolittle (1987) *J. Mol. Evol.* 35:351-360. The method used is similar to the method described by Higgins and Sharp (1989) *CABIOS* 5:151-153. The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. Using PILEUP, a reference sequence is compared to other test sequences to determine the percent sequence identity relationship using the following parameters: default gap weight (3.00), default gap length weight (0.10), and weighted end gaps. PILEUP can be obtained from the GCG sequence analysis software package, e.g., version 7.0 (Devereaux et al. (1984) *Nuc. Acids Res.* 12:387-395).

Another example of an algorithm that is suitable for determining percent sequence identity and sequence similarity are the BLAST and BLAST 2.0 algorithms, which are described in Altschul et al. (1977) *Nuc. Acids Res.* 25:3389-3402, and Altschul et al. (1990) *J. Mol. Biol.* 215:403-410, respectively. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always>0) and N (penalty score for mismatching residues; always<0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff (1989) *Proc. Natl. Acad. Sci. USA* 89:10915) alignments (B) of 50, expectation (E) of 10, M=5, N=−4, and a comparison of both strands.

The BLAST algorithm also performs a statistical analysis of the similarity between two sequences (see, e.g., Karlin and Altschul (1993) *Proc. Natl. Acad. Sci. USA* 90:5873-5787).

One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

The phrase "selectively (or specifically) hybridizes to" refers to the binding, duplexing, or hybridizing of a molecule only to a particular nucleotide sequence under stringent hybridization conditions when that sequence is present in a complex mixture (e.g., total cellular or library DNA or RNA).

The phrase "stringent hybridization conditions" refers to conditions under which a probe will hybridize to its target subsequence, typically in a complex mixture of nucleic acid, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For selective or specific hybridization, a positive signal is at least two times background, optionally 10 times background hybridization. Exemplary stringent hybridization conditions can be as following: 50% formamide, 5×SSC, and 1% SDS, incubating at 42° C., or 5×SSC, 1% SDS, incubating at 65° C., with wash in 0.2×SSC, and 0.1% SDS at 65° C. Such washes can be performed for 5, 15, 30, 60, 120, or more minutes.

Nucleic acids that do not hybridize to each other under stringent conditions are still substantially identical if the polypeptides that they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. Such washes can be performed for 5, 15, 30, 60, 120, or more minutes. A positive hybridization is at least twice background. Those of ordinary skill will readily recognize that alternative hybridization and wash conditions can be utilized to provide conditions of similar stringency.

The phrase "a nucleic acid sequence encoding" refers to a nucleic acid which contains sequence information for a structural RNA such as rRNA, a tRNA, or the primary amino acid sequence of a specific protein or peptide, or a binding site for a trans-acting regulatory agent. This phrase specifically encompasses degenerate codons (i.e., different codons which encode a single amino acid) of the native sequence or sequences which may be introduced to conform with codon preference in a specific host cell.

The term "reactive" means capable of binding or otherwise associating nonrandomly with a binding pair.

The term "label" refers to a composition detectable by spectroscopic, photochemical, biochemical, immunochemical, or chemical means. For example, useful labels include radioactive reagents, fluorescent dyes, electron-dense reagents, enzymes (e.g., as commonly used in ELISA), biotin, dioxigenin, or haptens and proteins for which antisera or monoclonal antibodies are available.

A "labeled antibody" is one that is bound, either covalently, through a linker, or through ionic, van der Waals or hydrogen bonds to a label such that the presence of the antibody may be detected by detecting the presence of the label bound to the antibody.

The phrase "complex" as used herein, refers to any distinct chemical species in which two or more identical or nonidentical chemical species (ionic or uncharged) are associated.

III. Affinity Agents of the Invention

The present invention provides affinity agents that are capable of specifically binding antibodies specific for SAP. The methods of the present invention employ affinity agents containing one or more SAP epitopes as binding reagents that specifically bind to antibodies to *B. anthracis*. Affinity agents can be, e.g., polypeptides, peptidomimetic compounds, or other molecules such as haptens that can be bound by an anti-SAP antibody. Polypeptides such as SAP polypeptides and polypeptide fragments thereof that contain at least one epitope specific for SAP are useful affinity agents. Polypeptides other than SAP that contain one or more SAP epitopes are useful affinity agents as well.

1. SAP Polypeptides

Peptides containing antigenic determinants of SAP can be produced by methods known to those of skill in the art. The amino acid sequence of a *B. anthracis* SAP polypeptide is provided as SEQ ID NO:1. A *B. anthracis* SAP polypeptide from a different strain is described in Etienne-Toumelin et al., J. Bacteriol. 177:614-620 (1995).

The SAP proteins, or subsequences thereof, may be synthesized using recombinant DNA methodology. Generally this involves creating a DNA sequence that encodes the polypeptide, modified as desired, placing the DNA in an expression cassette under the control of a particular promoter, expressing the protein in a host, isolating the expressed protein and, if required, renaturing the protein. Alternatively, endogenous SAP polypeptides can be isolated from *B. anthracis*.

SAP polypeptides can be expressed in a variety of host cells, including *E. coli*, other bacterial hosts, yeasts, filamentous fungi, and various higher eukaryotic cells such as the COS, CHO and HeLa cells lines and myeloma cell lines. Techniques for gene expression in microorganisms are described in, for example, Smith, *Gene Expression in Recombinant Microorganisms* (*Bioprocess Technology*, Vol. 22), Marcel Dekker, 1994. Examples of bacteria that are useful for expression include, but are not limited to, *Escherichia, Enterobacter, Azotobacter, Erwinia, Bacillus, Pseudomonas, Klebsielia, Proteus, Salmonella, Serratia, Shigella, Rhizobia, Vitreoscilla*, and *Paracoccus*. Filamentous fungi that are useful as expression hosts include, for example, the following genera: *Aspergillus, Trichoderma, Neurospora, Penicillium, Cephalosporium, Achlya, Podospora, Mucor, Cochliobolus*, and *Pyricularia*. See, e.g., U.S. Pat. No. 5,679,543 and Stahl and Tudzynski, Eds., *Molecular Biology in Filamentous Fungi*, John Wiley & Sons, 1992. Synthesis of heterologous proteins in yeast is well known and described in the literature. *Methods in Yeast Genetics*, Sherman, F., et al., Cold Spring Harbor Laboratory, (1982) is a well recognized work describing the various methods available to produce the enzymes in yeast.

SAP proteins, whether recombinantly or naturally produced, can be purified, either partially or substantially to homogeneity, according to standard procedures of the art, such as, for example, ammonium sulfate precipitation, affinity columns, column chromatography, gel electrophoresis and the like (see, generally, R. Scopes, *Protein Purification*, Springer-Verlag, N.Y. (1982), Deutscher, *Methods in Enzymology Vol.* 182*: Guide to Protein Purfication.*, Academic Press, Inc. N.Y. (1990)). Once purified, partially or to homogeneity as desired, the polypeptides can then be used (e.g., as affinity agents or as immunogens for antibody production).

One of skill in the art would recognize that after chemical synthesis, biological expression, or purification, the SAP protein(s) may possess a conformation substantially different than the native conformations of the constituent polypeptides. In this case, it may be necessary or desirable to denature and reduce the polypeptide and then to cause the polypeptide to re-fold into the preferred conformation. Methods of reducing and denaturing proteins and inducing re-folding are well known to those of skill in the art (See, Debinski et al. (1993) *J. Biol. Chem.* 268: 14065-14070; Kreitman and Pastan (1993) *Bioconjug. Chem.* 4: 581-585; and Buchner et al. (1992) *Anal. Biochem.* 205: 263-270). Debinski et al., for example, describe the denaturation and reduction of inclusion body proteins in guanidine-DTE. The protein is then refolded in a redox buffer containing oxidized glutathione and L-arginine.

One of skill also would recognize that modifications can be made to the SAP polypeptides without diminishing their antigenic activity. The SAP polypeptides need only contain one epitope specific for SAP. Polypeptides other than SAP that contain one or more SAP epitopes can be produced in the same way. Modifications can be made to facilitate the cloning, expression, or incorporation of the polypeptide into a fusion protein. Such modifications include, for example, a methionine added at the amino terminus to provide an initiation site, or additional amino acids (e.g., poly His) placed on either terminus to create conveniently located restriction sites or termination codons or purification sequences.

2. *B. anthracis* SAP-Encoding Nucleic Acids.

Nucleic acids that encode *B. anthracis* are useful for the recombinant production of SAP. Such nucleic acids can be isolated, for example, by routine cloning methods. The cDNA sequence provided in SEQ ID NO:2 can be used to provide probes that specifically hybridize to a SAP gene, to a SAP mRNA, or to a SAP cDNA in a cDNA library (e.g., in a Southern or Northern blot). Once the target SAP nucleic acid is identified, it can be isolated according to standard methods (see, e.g., Sambrook, Berger, and Ausubel, supra.).

SAP nucleic acids also can be isolated by amplification methods such as polymerase chain reaction (PCR), the ligase chain reaction (LCR), the transcription-based amplification system (TAS), the self-sustained sequence replication system (SSR) and other cloning and in vitro amplification methodologies. Examples of these techniques and instructions sufficient to direct persons of skill through many cloning exercises are found in Berger, Sambrook, and Ausubel (all supra.); Cashion et al., U.S. Pat. No. 5,017,478; and Carr, European Patent No. 0,246,864. Examples of techniques sufficient to direct persons of skill through in vitro amplification methods are found in Berger, Sambrook, and Ausubel, as well as Mullis et al. (1987) U.S. Pat. No. 4,683,202*; PCR Protocols A Guide to Methods and Applications* (Innis et al., eds) Academic Press Inc. San Diego, Calif. (1990) (Innis); Arnheim & Levinson (Oct. 1, 1990) C&EN 36-47*; The Journal Of NIH Research* (1991) 3: 81-94; (Kwoh et al. (1989) *Proc. Nat.'l. Acad. Sci. USA* 86: 1173; Guatelli et al. (1990) *Proc. Natl. Acad. Sci. USA* 87: 1874; Lomell et al. (1989) *J. Clin. Chem.* 35: 1826; Landegren et al. (1988) *Science* 241: 1077-1080; Van Brunt (1990) *Biotechnology* 8: 291-294; Wu and Wallace (1989) *Gene,* 4: 560; and Barringer et al. (1990) *Gene* 89: 117.

A polynucleotide that encodes a polypeptide containing an antigenic determinant of SAP, e.g., a SAP polypeptide such as SEQ ID NO:1, can be operably linked to appropriate expression control sequences for a particular host cell in which the polypeptide is to be expressed. Such constructs are often referred to as "expression cassettes." For *E. coli*, appropriate control sequences include a promoter such as the T7, trp, or lambda promoters, a ribosome binding site and preferably a transcription termination signal. For eukaryotic cells, the control sequences typically include a promoter which optionally includes an enhancer derived from immunoglobulin genes, SV40, cytomegalovirus, etc., and a polyadenylation sequence, and may include splice donor and acceptor sequences. In yeast, convenient promoters include GAL1,10 (Johnson and Davies (1984) *Mol. Cell. Biol.* 4:1440-1448) ADH2 (Russell et al. (1983) *J. Biol. Chem.* 258:2674-2682), PHO5 (*EMBO J.* (1982) 6:675-680), and MFocl (Herskowitz and Oshima (1982) in *The Molecular Biology of the Yeast Saccharomyces* (eds. Strathem, Jones, and Broach) Cold Spring Harbor Lab., Cold Spring Harbor, N.Y., pp. 181-209).

Expression cassettes are typically introduced into a vector that facilitates entry into a host cell, and maintenance of the expression cassette in the host cell. Vectors that include a polynucleotide that encodes a polypeptide containing a SAP epitope are provided by the invention. Such vectors often include an expression cassette that can drive expression of the SAP polypeptide. To easily obtain a vector of the invention, one can clone a polynucleotide that encodes the SAP polypeptide into a commercially or commonly available vector. A variety of common vectors suitable for this purpose are well known in the art. For cloning in bacteria, common vectors include pBR322 derived vectors such as PBLUESCRIPT™, and λ-phage derived vectors. In yeast, vectors include Yeast Integrating plasmids (e.g., YIp5) and Yeast Replicating plasmids (the YRp series plasmids) and pGPD-2. A multicopy plasmid with selective markers such as Leu-2, URA-3, Trp-1, and His-3 is also commonly used. A number of yeast expression plasmids such as YEp6, YEp13, YEp4 can be used as expression vectors. The above-mentioned plasmids have been fully described in the literature (Botstein et al. (1979) *Gene* 8:17-24; Broach et al. (1979) *Gene,* 8:121-133). For a discussion of yeast expression plasmids, see, e.g., Parents, B., *YEAST* (1985), and Ausubel, Sambrook, and Berger, all supra). Expression in mammalian cells can be achieved using a variety of commonly available plasmids, including pSV2, pBC12BI, and p91023, as well as lytic virus vectors (e.g., vaccinia virus, adenovirus, and baculovirus), episomal virus vectors (e.g., bovine papillomavirus), and retroviral vectors (e.g., murine retroviruses).

The nucleic acids that encode SAP polypeptides or other polypeptides containing SAP epitopes can be transferred into the chosen host cell by well-known methods such as calcium chloride transformation for *E. coli* and calcium phosphate treatment or electroporation for *E. coli* or mammalian cells. Cells transformed by the plasmids can be selected by resistance to antibiotics conferred by genes contained on the plasmids, such as the amp, gpt, neo and hyg genes, among others. Techniques for transforming fungi are well known in the literature and have been described, for instance, by Beggs et al. ((1978) *Proc. Natl. Acad. Sci. USA* 75: 1929-1933), Yelton et al. ((1984) *Proc. Natl. Acad. Sci. USA* 81: 1740-1747), and Russell ((1983) *Nature* 301: 167-169). Procedures for transforming yeast are also well known (see, e.g., Beggs (1978) *Nature* (London), 275:104-109; and Hinnen et al. (1978) *Proc. Natl. Acad. Sci. USA,* 75:1929-1933. Transformation and infection methods for mammalian and other cells are described in Berger and Kimmel, *Guide to Molecular Cloning Techniques, Methods in Enzymology* 152 Academic Press, Inc., San Diego, Calif. (Berger); Sambrook et al. (1989) *Molecular Cloning—A Laboratory Manual* (2nd ed.) Vol. 1-3, Cold Spring Harbor Laboratory, Cold Spring Harbor Press, NY, (Sambrook et al.); *Current Protocols in Molecular Biology*, F. M. Ausubel et al., eds., Current Protocols, a joint venture between Greene Publishing Associates, Inc. and John Wiley & Sons, Inc., (1994 Supplement) (Ausubel).

Once, peptides containing SAP epitopes are produced, they can be used as affinity agents to detect antibodies present in a biological sample.

IV. Detecting Antibody with an Affinity Agent

In the present invention, affinity agents are used to detect antibodies specific for *B. anthracis*. After assaying for antibodies to *B. anthracis* in a sample with an affinity agent, a diagnosis of anthrax infection can be made. If the affinity agent contacts antibodies specific for *B. anthracis* in a sample, a complex of affinity agent and antibodies will form. If antibodies specific for *B. anthracis* are not present in the sample, the affinity agent will not specifically bind to antibodies and no complex will form. The presence of the complex indicates exposure to *B. anthracis*.

The methods of the present invention employ different immunologic techniques and immunoassays, including Western blotting, to detect antibodies to *B. anthracis* in a sample. A general overview of the applicable technology can be found in Harlow & Lane, *Antibodies: A Laboratory Manual* (1988).

One method of detection is the enzyme-linked immunosorbent assay known as ELISA. In this method, antibodies in a sample are detected after the antibodies are specifically bound to an affinity agent on a solid support. A reagent (e.g., an affinity agent) that specifically binds to the antibodies can be non-diffusively immobilized on the support either by covalent or non-covalent methods, which are known to those of skill in the art. See, e.g., Pluskal et al. (1986) *Biotechniques* 4:272-283. Suitable supports include, for example, glasses, plastics, polymers, metals, metalloids, ceramics, organics, and the like. Specific examples, include, but are not limited to, microtiter plates, nitrocellulose membranes, nylon membranes, and derivatized nylon membranes, beads, and also particles, such as agarose, SEPHADEX™, and the like. Assay systems for use in the methods and kits of the invention include, but are not limited to, dipstick-type devices, immunochromatographic test strips and radial partition immunoassay devices, microtiter assays and flow-through devices. Where the solid support is a membrane, the test sample can flow through the membrane, for example, by gravity, capillary action, or under positive or negative pressure.

Once the affinity agent is immobilized on the solid support, the immobilized affinity agent is contacted with the sample suspected of containing the antibody. After a suitable reaction time, unbound components are removed by washing. An enzyme-conjugated secondary anti-isotype antibody is then added which binds to human immunoglobulins. The enzyme is preferably, but not limited to, either horseradish peroxidase, alkaline phosphatase, or beta-galactosidase. The enzyme is capable of converting a colorless or near colorless substrate or co-substrate into a highly colored product or a product capable of forming a colored complex with a chromogen. Alternatively, the detection system or assay may employ an enzyme which, in the presence of the proper substrate(s), emits light. The amount of product formed can be detected either visually, spectrophotometrically, electrochemically, or luminometrically, and is compared to a similarly treated control. The detection system may also employ radioactively labeled antibodies, in which case the amount of immune complex is quantified by scintillation counting or gamma counting.

Another method of detection is by competition assay. In competition assays, a sample, such as sera, from the subject is reacted with an affinity agent bound to a solid support which may be, for example, a plastic bead or tube or ELISA 96-well plate. Excess sera is washed away. A labeled (enzyme linked, fluorescent, radioactive, etc.) monoclonal antibody that binds to the affinity reagent is then contacted with the solid support. The amount of inhibition of monoclonal antibody binding is measured relative to a control in order to determine whether antibodies are present in the sera.

By the same token, antibodies that bind the affinity agent may be bound to the solid support. Labeled affinity agent may be mixed with suitable dilutions of the sample to be tested. This mixture is then brought into contact with the antibody bound to the solid support. After a suitable incubation period, the solid support is washed and the amount of labeled affinity agent is quantified. A reduction in the amount of label bound to the solid support is indicative of the presence of antibodies specific for the affinity agent in the original sample.

Another method of detection is the homogenous immunoassay. With this assay, there are many variations in design. By way of example, numerous possible configurations for homogeneous enzyme immunoassays and methods by which they may be performed are given in Tijssen, P., *Practice and Theory of immunoassays*, Elsevier Press, Amersham, Oxford, N.Y., 1985. Detection systems which may be employed include those based on enzyme channeling, bioluminescence, allosteric activation and allosteric inhibition. Methods employing liposome-entrapped enzymes or coenzymes may also be used (see e.g., Pinnaduwage, P. and Huang, L., *Clin. Chem.* (1988) 34/2: 268-272, and Ullmann, E. F. et al., *Clin Chem.* (1987) 33/9: 1579-1584.)

Another method of detection is the micro-agglutination assay. In this assay, latex beads, red blood cells or other agglutinable particles are coated with the affinity agent and mixed with a sample from the subject, such that antibodies in the sample that are specifically reactive with the affinity agent crosslink with the antigen, causing agglutination. The agglutinated affinity agent-antibody complexes form a precipitate, visible with the naked eye or by spectrophotometer.

Membrane-based detection methods may be used to detect antibodies to *B. anthracis*. These methods are described in, e.g., U.S. Pat. No. 5,922,615. These systems employ an apparatus that includes a porous member, such as a membrane or a filter, onto which is bound a multiplicity of affinity agents that specifically bind antibodies to *B. anthracis*. The apparatus also includes a non-absorbent member with a textured surface in communication with the lower surface of the porous member. The textured surface of the non-absorbent member can be a grooved surface (e.g., analogous to the surface of a record album) or it can be composed of channels, such that when the porous and non-absorbent members are brought into contact with one another a network of capillary channels is formed. The capillary network is formed from the contact of the porous member with the textured surface of the non-absorbent member and can be constructed either before or subsequent to the initial contacting of the porous member with a fluid.

In some embodiments, the capillary communication between the porous member and the non-absorbent member favors delaying the transferal of fluid from the porous member to the capillary network formed by the porous member and the textured surface of the non-absorbent member until the volume of the added fluid substantially exceeds the void volume of the porous member. The transferal of fluid from the porous member to the network of capillary channels formed by the porous member and the textured surface of the non-absorbent member can occur without the use of external means, such as positive external pressure or vacuum, or contact with an absorbent material.

An optional member which is placed in contact with the upper surface of the porous member may be used to partition the upper surface of the device into discrete openings. Such openings can access either the porous member or the textured surface of the non-absorbent second member. The optional member can in conjunction with the non-absorbent member compose a fluid receiving zone in which there is no intervening porous member. A fluid receiving zone constructed from the non-absorbent member and the optional member provides fluid capacity in addition to that provided by the network of capillary channels created by the contact of the porous member and the non-absorbent member. The openings in the optional member may include a first fluid opening and also an additional fluid opening. The first fluid opening functions as a portal for the introduction of the first fluid added to the device. The additional fluid opening serves as an additional portal through which additional fluids may be added to the inventive device.

To perform an assay using these devices, a volume of the test sample is added to the porous member, where the sample permeates the void volume of the porous member and thereby contacts the affinity agent immobilized on the porous member. In a non-competitive assay, the sample to be assayed is applied to the porous member and the antibodies, if present, are bound by the affinity agent. A detection reagent for the antibodies is then added as an additional fluid; these bind to the complex of the antibodies and affinity agent. An additional fluid containing reagents to effect a separation of free from bound labeled reagents can be added to remove excess detection reagent, if needed.

This device is designed to provide sufficient sensitivity to measure low concentrations of antibodies specific for SAP or for an antigenic determinant of SAP because one can use large amounts of sample and efficiently remove the excess of detection reagent. Indeed, the efficient separation of free from bound label achieved by the network of capillary channels of this device improves the discrimination of specific SAP antibodies-associated signal over non-specific background signal. If needed, a signal developer solution is then added to enable the label of the detection moiety to develop a detectable signal. The signal developed can then be related to the concentration of the target ligand within the sample. In one embodiment, the transfer of fluid between the porous first member of the device and the network of capillary channels formed by the contact of the porous member and textured surface of the non-absorbent second member of the device is generally self-initiated at the point when the total volume of fluid added to the device exceeds the void volume of the porous member, thus obviating the need for active interaction by the user to remove excess fluid from the analyte detection zone. This method enables the detection of antibodies specific for SAP in a manner that is simple, rapid, convenient, sensitive and efficient in the use of reagents.

The labels used in the detection systems allow detection by a variety of methods including but not limited to visual detection of a precipitate or color change, visual detection by microscopy, automated detection by spectrometry, radiometric measurement, sorting by flow cytometry, or the like. Examples of detectable labels include fluorescein and rhodamine (for fluorescence microscopy), horseradish peroxidase (for either light or electron microscopy and biochemical detection), biotin-streptavidin (for light or electron microscopy) and alkaline phosphatase (for biochemical detection by color change).

V. Antibody Response

An animal, e.g., a human, that is exposed to an antigenic determinant of *B. anthracis* will, at some time following exposure, begin making antibodies to *B. anthracis*. There are five classes of antibodies (IgM, IgG, IgD, IgE, IgA) that can be made in an immunogenic response to an antigen. All five classes of antibodies can be detected by the methods and kits of this invention. IgM is the first class of antibody to appear on the surface of a developing B cell. It is the first antibody produced in response to antigenic determinants. IgM antibodies are not secreted in large quantities and generally have low affinity, yet they are capable of efficiently binding antigen. In the early stages of a primary antibody response, IgM is the only antibody secreted into the blood. IgM antibodies are, therefore, indicative of recent antigenic exposure.

One of the first serological markers of anthrax infection in an animal is IgM antibodies specific for *B. anthracis*. The present invention provides methods for detecting IgM antibodies before clinical manifestation of disease in the animal. The affinity agents of this invention, i.e., SAP polypeptides, are capable of efficiently binding IgM antibodies present in a biological sample. In some animals, IgM antibodies may be the only class of antibodies present in the sample that indicate anthrax infection. Determination of anti-*B. anthracis* antibodies of the IgM class to *B. anthracis* is, therefore, useful for early detection of anthrax infection in an animal.

After producing IgM antibodies, antigen-stimulated B cells in an animal exposed to *B. anthracis* may produce IgD and IgG antibodies. Other antigen-stimulated cells may produce IgG, IgE or IgA antibodies. IgG, IgE and IgA molecules are referred to as secondary classes of antibodies. Another aspect of the present invention, therefore, is the detection of complexes between an affinity agent and antibodies other than IgM. The presence of IgG or other classes of antibodies bound to the affinity agent indicates the presence of anthrax exposure and infection in the animal.

Anti-Bacillus-anthracis antibodies may be detected before the onset of symptoms in the animal. In one embodiment of the invention, the anti-*B. anthracis* antibodies may be detected at least four days after exposure to anthrax. In another embodiment, the anti-*B. anthracis* antibodies may be detected up to 7 days after exposure to anthrax. In another embodiment, the anti-*B. anthracis* antibodies may be detected up to 14 days after exposure to anthrax. In yet another embodiment, the anti-*B. anthracis* antibodies may be detected between 4 and 14 days after exposure to anthrax. In another aspect, the anti-*B. anthracis* antibodies may be detected greater than 14 days after exposure to anthrax.

Biological samples to test for the presence of anthrax, i.e. testing for the presence of antibodies specific for an epitope of *B. anthracis* or testing for antigenic determinants of *B. anthracis*, can be collected using known methods. The sample can be taken directly from an animal or it can be in partially purified form or purified form. In one embodiment of the invention, blood drawn from a human is tested. In another embodiment, lymph fluids are tested.

VI. Capture Reagents

The present invention provides capture reagents that are capable of specifically binding SAP. Capture reagents can specifically bind SAP polypeptides, fragments of SAP polypeptides or polypeptides containing one or more SAP epitopes. Capture reagents can be antibodies specific for *Bacillus anthracis*. In addition, capture reagents are useful for identifying affinity agents that specifically bind to anti-SAP antibodies.

The present invention, therefore, employs antibodies to *B. anthracis* as capture reagents that specifically bind to *B. anthracis* epitopes in a sample. Capture reagents of the invention can be obtained, for example, using a *B. anthracis* SAP polypeptide as an immunogen. The entire SAP can be used as a capture reagent, or polypeptide subfragments that include an immunogenic epitope of SAP can be used. Suitable SAP polypeptides or fragments thereof can be isolated from *B. anthracis*, or more preferably can be produced using recombinant methods.

The invention provides capture reagents that can specifically bind *B. anthracis* SAP polypeptides or fragments thereof. Capture reagents can also be, for example, antibodies prepared using as immunogens, including natural, recombinant or synthetic polypeptides derived from *B. anthracis* SAP. The amino acid sequence of a *B. anthracis* SAP is shown as SEQ ID NO:1. Such polypeptides can function as immunogens that can be used for the production of monoclonal or polyclonal antibodies. Immunogenic peptides derived from SAP can also be used as immunogens; such peptides are sometimes conjugated to a carrier polypeptide prior to inoculation. Immunogens can be used in either pure or impure form. Production of antibodies against SAP polypeptides or polypeptides containing a SAP epitope is discussed in more detail below. Suitable capture reagents also include those that are obtained using methods such as phage display.

Various procedures known in the art can be used for the production of antibodies that specifically bind to a SAP epitope. For the production of polyclonal antibodies, one can use SAP to inoculate any of various host animals, including but not limited to rabbits, mice, rats, sheep, goats, and the like. The SAP polypeptide can be prepared by recombinant means as described above using an expression vector containing a nucleic acid that encodes the *B. anthracis* SAP. For example, a nucleotide sequence encoding a *B. anthracis* SAP beginning at approximately 30 amino acids from the published N-terminus (i.e., at the presumed cleavage sequence) is presented in SEQ ID NO:2.

Monoclonal antibodies can be prepared by any technique that provides for the production of antibody molecules by continuous cell lines in culture, including the hybridoma technique originally developed by Kohler and Milstein ((1975) *Nature* 256: 495-497), as well as the trioma technique, the human B-cell hybridoma technique (Kozbor et al. (1983) *Immunology Today* 4: 72), and the EBV-hybridoma technique to produce human monoclonal antibodies (Cole et al. (1985) in *Monoclonal Antibodies and Cancer Therapy*, Alan R. Liss, Inc., pp. 77-96). Monoclonal antibodies also can be produced in germ-free animals as was described in PCT/US89/02545 (Publication No. WO8912690, published Dec. 12, 1989) and U.S. Pat. No. 5,091,512.

Fragments of antibodies are also useful as capture reagents. While various antibody fragments can be obtained by the digestion of an intact antibody, one of skill will appreciate that such fragments may be synthesized de novo either chemically or by utilizing recombinant DNA methodology. Thus, the term "antibody," as used herein, also includes antibody fragments either produced by the modification of whole antibodies or those synthesized de novo using recombinant DNA methodologies (e.g., single chain Fv). Single chain antibodies are also useful to construct detection moieties. Methods for producing single chain antibodies were described in, for example, U.S. Pat. No. 4,946,778. Techniques for the construction of Fab expression libraries were described by Huse et al. (1989) *Science* 246: 1275-1281; these techniques facilitate rapid identification of monoclonal Fab fragments with the desired specificity for SAP. Suitable capture reagents also include those that are obtained using methods such as phage display.

To prepare a suitable antigen preparation, one can prepare an expression library from *B. anthracis* and screen the library with a polyclonal antibody that is raised against a crude preparation of SAP. The inserts from those expression plasmids that express the SAP are then subcloned and sequenced. The SAP-encoding inserts are cloned into an expression vector and used to transform *E. coli* or other suitable host cells. The resulting preparation of recombinant SAP is then used to inoculate an animal, e.g., a mouse.

In one embodiment, the capture reagents are recombinantly produced polyclonal or monoclonal antibodies that bind to SAP. Recombinant antibodies are typically produced by immunizing an animal with SAP, obtaining RNA from the spleen or other antibody-expressing tissue of the animal, making cDNA, amplifying the variable domains of the heavy and light immunoglobulin chains, cloning the amplified DNA into a phage display vector, infecting *E. coli*, expressing the phage display library, and selecting those library members that express an antibody that binds to SAP. Methods suitable for carrying out each of these steps are described in, for example U.S. Pat. No. 6,057,098. In another embodiment, the antibody or other binding peptides are expressed on the surface of a replicable genetic unit, such as a filamentous phage, and especially phage M13, Fd and F1. Most work has inserted libraries encoding polypeptides to be displayed with either pIII or pVIII of these phage, forming a fusion protein which is displayed on the surface of the phage. See, e.g., Dower, WO 91/19818; Devlin, WO 91/18989; MacCafferty, WO 92/01047 (gene III); Huse, WO 92/06204; Kang, WO 92/18619 (gene VIII). In one embodiment, the genes that encode the heavy and light chains of antibodies present in the cDNA library are amplified using a set of primers that can amplify substantially all of the different heavy and light chains. The resulting amplified fragments that result from the amplification step are pooled and subjected to asymmetric PCR so that only one strand (e.g., the antisense strand) is amplified. The single strand products are phosphorylated, annealed to a single-stranded uracil template (e.g., the vector BS45, described in U.S. Pat. No. 6,057,098, which has coding regions for the constant regions of mouse heavy and light chains), and introduced into a uracil DNA glycosylase$^+$ host cell to enrich for vectors that contain the coding sequences for heavy and light chain variable domains.

To screen for phage that express an antibody that binds to SAP, one can attach a label to SAP using methods known to those of skill in the art. In one aspect of the invention, the phage that display such antibodies are selected using SAP to which is attached an immobilizable tag, e.g., biotin. The phage are contacted with the biotinylated antigen, after which the phage are selected by contacting the resulting complex with avidin attached to a magnetic latex bead or other solid support. The selected phage are then plated, and may be screened with SAP to which is attached a detectable label.

In one embodiment, the library is enriched for those phage that display more than one antibody that binds to SAP. Methods and vectors that are useful for this enrichment are described in U.S. Pat. No. 6,057,098. The panning can be repeated one or more times to enhance the specificity and sensitivity of the resulting antibodies. Preferably, panning is continued until the percentage of functional positives is at least about 70%, more preferably at least about 80%, and most preferably at least about 90%.

A recombinant anti-SAP monoclonal antibody can then be selected by amplifying antibody-encoding DNA from individual plaques, cloning the amplified DNA into an expression vector, and expressing the antibody in a suitable host cell (e.g., $E.\ coli$). The antibodies are then tested for ability to bind SAP.

Recombinant polyclonal antibodies are used because of the various forms of SAP that may be found in clinical samples due to, for example, proteolysis. The diverse fine binding specificity of members of a population of polyclonal antibodies often allows the population to bind to several forms of SAP (e.g., species variants, escape mutant forms, proteolytic fragments) to which a monoclonal reagent may be unable to bind. Methods for producing recombinant polyclonal antibodies are described in U.S. Pat. No. 6,057,098. Specific methods of producing recombinant polyclonal antibodies that bind to SAP are described in the Examples below.

Polyclonal antibodies can be prepared as described above, except that an individual antibody is not selected. The phage may be enriched for those that display more than one copy of the respective antibodies. The phage are then selected for those that bind to SAP. For example, one can use a biotinylated anti-SAP monoclonal antibody and SAP to concentrate those phage that express antibodies that bind to SAP. The biotinylated monoclonal antibody is immobilized on a solid support (e.g., magnetic latex) to which is attached avidin. The phage that are bound to the immobilized SAP are eluted, plated, and the panning repeated until the desired percentage of functional positives is obtained.

Once the capture reagents of this invention are produced, they can be used to detect SAP present in a biological sample.

VII. Detecting SAP Antigenic Determinants or SAP Polypeptides with a Capture Reagent As well as providing a method for detecting antibodies specific for $B.\ anthracis$ in a biological sample, the present invention also provides methods for the detection of SAP in a sample.

Biological samples to test for the presence of SAP in the sample are collected using the same methods for the collection of biological samples to test for the presence of antibodies specific for SAP in the sample. The sample can be taken directly from an animal or it can be in partially purified form or purified form. In one embodiment of the invention, the biological sample collected is fractionated into two samples. One sample is used to test for the presence of SAP in the sample and the other is used to test for the presence of antibodies specific for SAP in the sample.

In order to detect SAP in a sample, the present invention provides contacting the biological sample with a capture reagent, e.g., antibodies to a $B.\ anthracis$ surface array protein, under suitable reaction conditions. If a $B.\ anthracis$ surface array protein or epitopes thereof are present in the sample, a complex of protein and capture reagent will form. Formation of a complex indicates that the animal from which the sample was obtained was exposed to anthrax.

The present invention can detect $B.\ anthracis$ in a biological sample when present in the sample at a concentration of about $10^4$ cfu/ml or less. Preferably, the detection limit for $B.\ anthracis$ will be about $5 \times 10^3$ cfu/ml or less, more preferably about $1.8 \times 10^3$ cfu/ml or less, and still more preferably about $10^3$ cfu/ml or less.

SAP polypeptides or SAP antigenic determinants present in a sample can be detected by the methods of the invention before the onset of symptoms in the animal. In one embodiment of the invention, the SAP polypeptides or SAP antigenic determinants may be detected one day after exposure to anthrax. In another embodiment, the SAP polypeptides or SAP antigenic determinants may be detected up to 7 days after exposure to anthrax. In another embodiment, the SAP polypeptides or SAP antigenic determinants may be detected up to 14 days after exposure to anthrax. In yet another embodiment, the SAP polypeptides or SAP antigenic determinants may be detected greater than 14 days after exposure to anthrax.

The methods of the present invention employ different immunologic techniques and immunoassays to detect $B.\ anthracis$ SAP in a sample. The $B.\ anthracis$ detection methods of the present invention, like the $B.\ anthracis$ antibody detection methods, can be carried out in a wide variety of assay formats. In one embodiment, the assay methods involve immobilization of a capture reagent for $B.\ anthracis$ SAP on a solid support, followed by detection of the immobilized or bound SAP. The detectable labels can be detected directly after immobilization on the solid support, for example, or indirectly by an enzymatic or other reaction that results in a detectable change in a reactant that is present in the detection assay reaction.

One method of detection is based on the ELISA method. See, e.g., Elder et al., $J.\ Clin.\ Microbiol.$ 16:141 (1982); Ausubel et al., supra. Generally, antigens or capture reagents for antigens are fixed to a solid surface. Bound antigens are detected using antigen-specific antibodies that are detected by way of an enzymatic reaction. In one embodiment, the ELISA method used is the "sandwich" method wherein the antigens are bound to the solid surface via capture reagent bound to the solid surface. An antibody, or other antigen detection reagent, typically linked to an enzyme, is then contacted to the antigen, washed, then contacted with the enzyme substrate to select binding. These and other embodiments of the ELISA method are taught in, for example, Ausubel et al. § 11.2, supra.

To immobilize SAP on the solid support, a capture reagent that specifically binds to SAP is non-diffusively associated with the support. The capture reagents can be immobilized on the support either by covalent or non-covalent methods, which are known to those of skill in the art. See, e.g., Pluskal et al. (1986) *BioTechniques* 4: 272-283. Suitable supports include, for example, glasses, plastics, polymers, metals, metalloids, ceramics, organics, and the like. Specific examples include, but are not limited to, microtiter plates, nitrocellulose membranes, nylon membranes, and derivatized nylon membranes, beads, and also particles, such as agarose, SEPHADEX™, and the like. Assay systems for use in the methods and kits of the invention include, but are not limited to, dipstick-type devices, immunochromatographic test strips and radial partition immunoassay devices, microtiter assays and flow-through devices. Conveniently, where the solid support is a membrane, the test sample can flow through the membrane, for example, by gravity, capillary action, or under positive or negative pressure.

Once the sample has been contacted with the solid support, the solid support is then contacted with detection reagents for SAP. The solid support can be washed prior to contact with detection reagents to remove unbound reagents and test sample components. After incubation of the detection reagents for a sufficient time to bind a substantial portion of the immobilized SAP, any unbound labeled reagents are removed by, for example, washing. The detectable label associated with the detection reagents is then detected. For example, in the case of an enzyme used as a detectable label, a substrate for the enzyme that turns a visible color upon action of the enzyme is placed in contact with the bound detection reagent. A visible color will then be observed in proportion to the amount of the specific antigen in the sample.

Other detection systems, such as those described for detecting antibody with an affinity agent, for e.g., Western blotting, can be adapted to detect antigen with a capture reagent, including membrane-based detection methods. Any of the assays described herein can be used to confirm the results of another assay.

VIII. Detection Reagents

As discussed above, the presence of SAP can be detected using a detection reagent that is composed of a binding moiety that specifically binds to SAP. In addition, anti-SAP antibodies in a biological sample specific for SAP are generally detected using an antibody, or other capture reagent, that specifically binds to the anti-SAP antibodies, or complex of anti-SAP antibodies and affinity agent, in the sample. The detection reagents are either directly labeled, i.e., comprise or react to produce a detectable label, or are indirectly labeled, i.e., bind to a molecule that is itself labeled with a detectable label. Labels can be directly attached to or incorporated into the detection reagent by chemical or recombinant methods.

In one embodiment, a label is coupled to a molecule, such as an antibody that specifically binds to SAP, through a chemical linker. In another embodiment, a label is coupled to an antibody that specifically binds to human antibodies to SAP. Linker domains are typically polypeptide sequences, such as poly-Gly sequences of between about 5 and 200 amino acids (SEQ ID NO:5). In some embodiments, proline residues are incorporated into the linker to prevent the formation of significant secondary structural elements by the linker. Linkers may be flexible amino acid subsequences that are synthesized as part of a recombinant fusion protein comprising the RNA recognition domain. In one embodiment, the flexible linker is an amino acid subsequence that includes a proline, such as Gly(x)-Pro-Gly(x) (SEQ ID NO:6) where x is a number between about 3 and about 100. In other embodiments, a chemical linker is used to connect synthetically or recombinantly produced recognition and labeling domain subsequences. Such flexible linkers are known to persons of skill in the art. For example, poly(ethylene glycol) linkers are available from Shearwater Polymers, Inc. Huntsville, Ala. These linkers optionally have amide linkages, sulfhydryl linkages, or heterofunctional linkages.

The detectable labels used in the assays of the present invention, which are attached to the antibodies, can be primary labels (where the label comprises an element that is detected directly or that produces a directly detectable element) or secondary labels (where the detected label binds to a primary label, e.g., as is common in immunological labeling). An introduction to labels, labeling procedures and detection of labels is found in Polak and Van Noorden (1997) *Introduction to Immunocytochemistry,* 2nd ed., Springer Verlag, NY and in Haugland (1996) *Handbook of Fluorescent Probes and Research Chemicals*, a combined handbook and catalogue Published by Molecular Probes, Inc., Eugene, Oreg. Patents that described the use of such labels include U.S. Pat. Nos. 3,817,837; 3,850,752; 3,939,350; 3,996,345; 4,277,437; 4,275,149; and 4,366,241.

Primary and secondary labels can include undetected elements as well as detected elements. Useful primary and secondary labels in the present invention can include spectral labels such as green fluorescent protein, fluorescent dyes (e.g., fluorescein and derivatives such as fluorescein isothiocyanate (FITC) and Oregon Green™, rhodamine and derivatives (e.g., Texas red, tetrarhodimine isothiocynate (TRITC), etc.), digoxigenin, biotin, phycoerythrin, AMCA, CyDyes™, and the like), radiolabels (e.g., $^3$H, $^{125}$I, $^{35}$S, $^{14}$C, $^{32}$P, $^{33}$P, etc.), enzymes (e.g., horse radish peroxidase, alkaline phosphatase etc.), spectral colorimetric labels such as colloidal gold or colored glass or plastic (e.g. polystyrene, polypropylene, latex, etc.) beads. The label can be coupled directly or indirectly to a component of the detection assay (e.g., the detection reagent) according to methods well known in the art. As indicated above, a wide variety of labels may be used, with the choice of label depending on sensitivity required, ease of conjugation with the compound, stability requirements, available instrumentation, and disposal provisions.

Labels include those that use: 1) chemiluminescence (using horseradish peroxidase and/or alkaline phosphatase with substrates that produce photons as breakdown products as described above) with kits being available, e.g., from Molecular Probes, Amersham, Boehringer-Mannheim, and Life Technologies/Gibco BRL; 2) color production (using both horseradish peroxidase and/or alkaline phosphatase with substrates that produce a colored product (kits available from Life Technologies/Gibco BRL, and Boehringer-Mannheim)); 3) fluorescence using, e.g., an enzyme such as alkaline phosphatase, together with the substrate AttoPhos (Amersham) or other substrates that produce fluorescent products, 4) fluorescence (e.g., using Cy-5 (Amersham), fluorescein, and other fluorescent tags); 5) radioactivity. Other methods for labeling and detection will be readily apparent to one skilled in the art.

For use of the present invention outside the laboratory, labels are non-radioactive and readily detected without the necessity of sophisticated instrumentation. Preferably, detection of the labels will yield a visible signal that is immediately discernable upon visual inspection. One example of detectable secondary labeling strategies uses an antibody that recognizes SAP in which the antibody is linked to an enzyme (typically by recombinant or covalent chemical bonding). The antibody is detected when the enzyme reacts with its substrate, producing a detectable product. Enzymes that can be conjugated to detection reagents of the invention include, e.g., β-galactosidase, luciferase, horse radish peroxidase, and alkaline phosphatase. The chemiluminescent substrate for luciferase is luciferin. One embodiment of a fluorescent substrate for β-galactosidase is 4-methylumbelliferyl-β-D-galactoside. Embodiments of alkaline phosphatase substrates include p-nitrophenyl phosphate (pNPP), which is detected with a spectrophotometer; 5-bromo-4-chloro-3-indolyl phosphate/nitro blue tetrazolium (BCIP/NBT) and fast red/napthol AS-TR phosphate, which are detected visually; and 4-methoxy-4-(3-phosphonophenyl) spiro[1,2-d]oxetane-3,2'-adamantane], which is detected with a luminometer. Embodiments of horse radish peroxidase substrates include 2,2'azino-bis(3-ethylbenzthiazoline-6 sulfonic acid) (ABTS), 5-aminosalicylic acid (5AS), o-dianisidine, and o-phenylenediamine (OPD), which are detected with a spectrophotometer; and 3,3,5,5'-tetramethylbenzidine (TMB), 3,3'diaminobenzidine (DAB), 3-amino-9-ethylcarbazole (AEC), and 4-chloro-1-naphthol (4C1N), which are detected visually. Other suitable substrates are known to those skilled in the art. The enzyme-substrate reaction and product detection are performed according to standard procedures known to those skilled in the art and kits for performing enzyme immunoassays are available as described above.

The presence of a label can be detected by inspection, or a detector which monitors a particular probe or probe combination can be used to detect the detection reagent label. Typical detectors include spectrophotometers, phototubes and photodiodes, microscopes, scintillation counters, cameras, film and the like, as well as combinations thereof. Examples of suitable detectors are widely available from a variety of commercial sources known to persons of skill. Commonly, an optical image of a substrate comprising bound labeling moieties is digitized for subsequent computer analysis.

IX. Kits for the Detection of SAP

This invention also provides kits for the detection and/or quantification of anthrax using the methods described herein. The kits can include a container containing one or more of the above-discussed reagents with or without labels, either free or bound to solid supports. A suitable solid support, such as a membrane, can also be included in the kits of the invention. The kits can provide solid supports in the form of an assay apparatus that is adapted to use in the described assay. Preferably, the kits will also include reagents used in the described assays, including reagents useful for detecting the presence of the detectable labels. Other materials useful in the performance of the assays can also be included in the kits, including test tubes, transfer pipettes, and the like. The kits can also include written instructions for the use of one or more of these reagents in any of the assays described herein.

The kits of the invention can also include an internal and/or an external control. An internal control can consist of the SAP polypeptide or an anti-SAP antibody. The control antigen can conveniently be preattached to a capture reagent in a zone of the solid support adjacent to the zone to which the sample is applied. The external control can also consist of a SAP polypeptide or an anti-SAP antibody. In some embodiments, the antigen present in the external control will be at a concentration at or above the sensitivity limit of the assay means. The external control antigen can be diluted in the sample diluent and assayed in the same manner as would a biological sample. Alternatively, the external control SAP polypeptide or anti-SAP antibody can be added to an aliquot of an actual biological sample to determine the sensitivity of the assay. The kits of the present invention can contain material sufficient for one assay, or can contain sufficient materials for multiple assays.

All publications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

EXAMPLES

The following examples are offered to illustrate, but not to limit the present invention.

Example 1

Isolation of a Gene Encoding *Bacillus anthracis* Surface Array Protein (Sap)

This Example describes the cloning and characterization of a gene that encodes a *Bacillus anthracis* surface array protein (SAP).

Isolation OF *B. anthracis* DNA

*Bacillus anthracis* genomic DNA isolated from the non-pathologic Sterne strain was used as a template source for PCR amplification of a nucleic acid that codes for SAP. A total of 6 ml of *Bacillus anthracis* Sterne strain ($1\times10^{10}$/ml in PBS pH 7.4) was pelleted in a microcentrifuge at 10,000 g for 5 minutes. Bacterial pellets were then combined and resuspended in a final volume of 1 ml lysis buffer (50 mM Tris (hydroxymethyl)aminomethane ("Tris") pH 7.8, 10 mM ethylenediaminetetraacetic acid ("EDTA"), 100 μg/ml Ribonuclease (RNase A) (Roche Molecular Biochemical, Indianapolis, Ind.), 0.5% Triton X-100M (T-octylphenoxypolyethoxyethanol) (Sigma, St. Louis, Mo.), 12.5% sucrose). Lysozyme (Sigma) was added to a final concentration of 2 mg/ml and the mixture incubated for 1 hr at 37° C. 300 μg of Proteinase K (Roche Molecular Biochemical, Indianapolis, Ind.) and a one-tenth volume of 10% SDS was added to the mixture followed by a 1 hr incubation at 56° C. NaCl was then added to a final concentration of 500 mM by adding one-tenth volume of 5 M NaCl. The mixture was then twice extracted with phenol/chloroform (phenol:chloroform:isoamyl alcohol (50:49:1)) and the DNA in the aqueous layer sheared by passing the solution through an 18 gauge needle. DNA was precipitated with 2.5 volumes of ethanol and resuspended in 200 μl of distilled water. This DNA preparation was extracted once with Tris pH 8 equilibrated phenol, two times with phenol/chloroform and finally twice with chloroform (chloroform:isoamyl alcohol (49:1)) alone. DNA in the aqueous layer was precipitated a final time and resuspended in 500 μl of distilled water, yielding approximately 79 μg of DNA at 158 μg/ml. This DNA was used as a template in the subsequent PCR amplification of the SAP gene.

Cloning of *Bacillus anthracis* Sap Gene Via PCR Appropriate PCR primers were made corresponding to the coding sequence of the 5' and 3' ends of the *B. anthracis* SAP gene (see primer sequence below). These primers were based on a published nucleotide sequence (Etienne-Toumelin et al., supra). DNA encoding the native signal sequence of SAP (amino acids 1-29) was purposefully omitted from the cloning since a functional signal sequence was provided by the expression vector pBRncoH3 (described in copending, commonly-owned U.S. patent application Ser. No. 08/835,159, filed Apr. 4, 1997). The 5' primer contains 23 bases of vector sequence at its 5'-end that corresponds to the 3'-end of the pBRncoH3 vector. The 3' primer contains 19 bases of the tetracycline promoter, removed by HindIII digestion in the vector, in addition to 20 bases of vector sequence 3' to the HindIII site. The 3' primer was also engineered to encode a hexahistidine (SEQ ID NO:7) amino acid tag at the C-terminus of the SAP protein to allow for efficient purification using nickel-chelate affinity chromatography (see below).

5' PCR primer: 5'-TCGCTGCCCAACCAGCCATGGCCG-CAGGTAAAA CATTCCCAGAC-3' (SEQ ID NO:3)

3' PCR primer: 5'-GTGATAAACTACCGCATTAAAGCT-TATCGATGATA AGCTGTCAATTAGTGATGGT-GATGGTGATGTTTTG TTGCAGGTTTTGCTTCTTT-3' (SEQ ID NO:4)

The nucleic acid that encodes SAP was amplified using these primers and approximately 30 ng of *Bacillus anthracis* genomic DNA as template. The amplification was performed using Expand™ DNA polymerase (Roche Molecular Biochemical (Indianapolis, Ind.). SAP insert DNA (~300 ng) was purified and annealed to the HindIII-digested pBRncoH3 vector (100 ng) at a 6:1 molar ratio of insert to vector. An aliquot was electroporated into 40 μl of electrocompetent *E. coli* strain DH10B as described in Example 3. Various dilutions of the transformed cells were plated on LB agar plates supplemented with tetracycline (10 μg/ml) and grown overnight at 37° C. Three colonies were each picked into 3 ml 2xYT, supplemented with tetracycline (10 μg/ml), and grown overnight at 37° C. The following day, glycerol freezer stocks were made for long term storage at −80° C.

In order to confirm that the SAP gene had indeed been cloned, each of the three clones was tested for the ability to synthesize SAP protein upon arabinose induction as described below. All three clones produced a protein of the predicted size, approximately 94 kDa in molecular mass, and were shown to react with a rabbit anti-anthracis polyclonal serum using Western blot analysis (data not shown). Two of the three clones were sequenced and compared against the National Center for Biotechnology Information's (NCBI) non-redundant nucleotide database using the BLAST search engine. This search indicated that a SAP gene had indeed been cloned. There were eight differences in the predicted amino acid sequence compared to the noted published sequence. These changes are lysine 264 to arginine, glutamic acid 478 to alanine, arginine 482 to histidine, glutamic acid 496 to aspartic acid, lysine 556 to arginine, glutamic acid 606 to aspartic acid, lysine 607 to threonine, and valine 751 to alanine. Amino acid numbering is based on the published sequence (Etienne-Toumelin et al., supra). These differences may be due to the fact that a different *Bacillus anthracis* strain was used in the work described here. The original published work did not use the Sterne strain. The predicted amino acid sequence of the SAP gene cloned here shows 8 amino acid differences out of 785, and is thus 99.0% identical to the published sequence.

Example 2

Expression and Purification of Recombinant *Bacillus anthracis* SAP from *E. coli*

This Example describes the expression and purification of *B. anthracis* SAP using *E. coli*.

A shake flask containing 2xYT supplemented with 1% glycerol was inoculated with an *E. coli* DH10B strain from Example 1 that contained a cloned *B. anthracis* SAP gene and incubated overnight in an Innova 4330 incubator shaker (New Brunswick Scientific, Edison, N.J.) set at 37° C., 300 rpm. The inoculum was used to seed 500 mL cultures of defined medium (Pack et al. (1993) *Bio/Technology* 11: 1271-1277) supplemented with 3 g/L L-leucine, 3 g/L L-isoleucine, 12 g/L casein digest (Difco, Detroit, Mich.), 12.5 g/L glycerol and 10 μg/ml tetracycline. Cultures were grown in 2 L Tunair shake flasks (Shelton Scientific, Shelton, Conn.) at 37° C. and 300 rpm. Cells were grown to an optical density of approximately 4 absorption units at 600 nm. Expression of SAP was then induced by addition of L(+)-arabinose to 2 g/L during this logarithmic growth phase. The flasks were then maintained at 23° C. and 300 rpm overnight.

The following morning, bacterial cultures were passed through an M-110Y Microfluidizer (Microfluidics, Newton, Mass.) at 17,000 psi. The homogenate was clarified in a J2-21 centrifuge (Beckman, Fullerton, Calif.) and recombinant SAP purified from the supernatant using immobilized metal affinity chromatography. Briefly, Chelating Sepharose Fast-Flow™ resin (Pharmacia, Piscataway, N.J.) was charged with 0.1 M $NiCl_2$ and equilibrated in 20 mM borate, 150 mM NaCl, 10 mM imidazole, 0.01% $NaN_3$, pH 8. A stock solution was used to bring the supernatant concentration to 10 mM imidazole, pH 8. Chelating resin was then added to the supernatant and the mixture shaken for 1 hour at room temperature, 150-200 rpm. During this time, SAP was captured by means of the high affinity interaction between nickel and the hexahistidine tag engineered onto the C-terminus of SAP. After 1 hour, the resin mixture was poured into a chromatography column and washed with 20 mM borate, 150 mM NaCl, 10 mM imidazole, 0.01% $NaN_3$, pH 8.0. SAP was eluted from the resin with the same buffer containing 200 mM imidazole instead of 10 mM.

The volume of eluted SAP was reduced using a centrifuge concentrator with a 30 kDa molecular weight cut off (Amicon, Beverly, Mass.), and the sample subsequently dialyzed against sterile phosphate-buffered solution (PBS) for immunizations and BBS (20 mM borate, 150 mM NaCl, 0.01% $NaN_3$, pH 8.0) for biotinylation. Isolated SAP was evaluated for purity by SDS-PAGE analysis and shown to be greater than 95% pure. The protein concentration of recombinant SAP was determined by UV absorbance at 280 nm, assuming an absorbance of 0.593 for a 1 mg/ml solution.

Example 3

Construction of a Phage-Display Library

This Example describes the construction of a phage display library from which binding reagents that are specific for *B. anthracis* SAP were identified.

Immunization and mRNA Isolation

A phage display library for identification of SAP-binding molecules was constructed as follows. A/J mice (Jackson Laboratories, Bar Harbor, Me.) were immunized intraperitoneally with recombinant SAP antigen, using 100 μg protein in Freund's complete adjuvant, on day 0, and with 100 µg antigen on day 28. Test bleeds of mice were obtained through puncture of the retro-orbital sinus. If, by testing the titers, they were deemed high by ELISA using biotinylated SAP antigen immobilized via neutravidin (Reacti-Bind™ NeutrAvidin™-Coated Polystyrene Plates, Pierce, Rockford, Ill.), the mice were boosted with 100 µg of protein on day 70, 71 and 72, with subsequent sacrifice and splenectomy on day 77. If titers of antibody were not deemed satisfactory, mice were boosted with 100 µg antigen on day 56 and a test bleed taken on day 63. If satisfactory titers were obtained, the animals were boosted with 100 µg of antigen on day 98, 99, and 100 and the spleens harvested on day 105.

The spleens were harvested in a laminar flow hood and transferred to a petri dish, trimming off and discarding fat and connective tissue. The spleens were macerated quickly with the plunger from a sterile 5 cc syringe in the presence of 1.0 ml of solution D (25.0 g guanidine thiocyanate (Boehringer Mannheim, Indianapolis, Ind.), 29.3 ml sterile water, 1.76 ml 0.75 M sodium citrate pH 7.0, 2.64 ml 10% sarkosyl (Fisher Scientific, Pittsburgh, Pa.), 0.36 ml 2-mercaptoethanol (Fisher Scientific, Pittsburgh, Pa.)). This spleen suspension was pulled through an 18 gauge needle until all cells were lysed and the viscous solution was transferred to a microcentrifuge tube. The petri dish was washed with 1001 of solution D to recover any remaining spleen. This suspension was then pulled through a 22 gauge needle an additional 5-10 times.

The sample was divided evenly between two microcentrifuge tubes and the following added, in order, with mixing by inversion after each addition: 50 µl 2 M sodium acetate pH 4.0, 0.5 ml water-saturated phenol (Fisher Scientific, Pittsburgh, Pa.), 100 µl chloroform/isoamyl alcohol 49:1 (Fisher Scientific, Pittsburgh, Pa.). The solution was vortexed for 10 seconds and incubated on ice for 15 min. Following centrifugation at 14 krpm for 20 min at 2-8° C., the aqueous phase was transferred to a fresh tube. An equal volume of water saturated phenol:chloroform:isoamyl alcohol (50:49:1) was added, and the tube vortexed for ten seconds. After a 15 min incubation on ice, the sample was centrifuged for 20 min at 2-8° C., and the aqueous phase transferred to a fresh tube and precipitated with an equal volume of isopropanol at −20° C. for a minimum of 30 min. Following centrifugation at 14 krpm for 20 min at 4° C., the supernatant was aspirated away, the tubes briefly spun and all traces of liquid removed from the RNA pellet.

The RNA pellets were each dissolved in 300 µl of solution D, combined, and precipitated with an equal volume of isopropanol at −20° C. for a minimum of 30 min. The sample was centrifuged 14 krpm for 20 min at 4° C., the supernatant aspirated as before, and the sample rinsed with 100 µl of ice-cold 70% ethanol. The sample was again centrifuged 14 krpm for 20 min at 4° C., the 70% ethanol solution aspirated, and the RNA pellet dried in vacuo. The pellet was resuspended in 100 µl of sterile diethyl pyrocarbonate-treated water. The concentration was determined by $A_{260}$ using an absorbance of 1.0 for a concentration of 40 µg/ml. The RNAs were stored at −80° C.

Preparation of Complementary DNA (cDNA)

The total RNA purified from mouse spleens as described above was used directly as template for cDNA preparation. RNA (50 µg) was diluted to 100 µL with sterile water, and 10 µL of 130 ng/µL oligo $dT_{12}$ (SEQ ID NO:8) (synthesized on Applied Biosystems Model 392 DNA synthesizer) was added. The sample was heated for 10 min at 70° C., then cooled on ice. Forty µL 5× first strand buffer was added (Gibco/BRL, Gaithersburg, Md.), along with 20 µL 0.1 M dithiothreitol (Gibco/BRL, Gaithersburg, Md.), 10 µL 20 mM deoxynucleoside triphosphates (dNTP's, Boehringer Mannheim, Indianapolis, Ind.), and 10 µL water on ice. The sample was then incubated at 37° C. for 2 min. Ten µL reverse transcriptase (Superscript™ II, Gibco/BRL, Gaithersburg, Md.) was added and incubation was continued at 37° C. for 1 hr. The cDNA products were used directly for polymerase chain reaction (PCR).

Amplification of Antibody Genes by PCR

To amplify substantially all of the H and L chain genes using PCR, primers were chosen that corresponded to substantially all published sequences. Because the nucleotide sequences of the amino termini of H and L contain considerable diversity, 33 oligonucleotides were synthesized to serve as 5' primers for the H chains, and 29 oligonucleotides were synthesized to serve as 5' primers for the kappa L chains as described in U.S. patent application Ser. No. 08/835,159, filed Apr. 4, 1997. The constant region nucleotide sequences for each chain required only one 3' primer for the H chains and one 3' primer for the kappa L chains.

A 50 µL reaction was performed for each primer pair with 50 pmol of 5' primer, 50 µmol of 3' primer, 0.25 µL Taq DNA Polymerase (5 units/µL, Boehringer Mannheim, Indianapolis, Ind.), 3 µL cDNA (prepared as described in Example 3), 5 µL 2 mM dNTP's, 5 µL 10× Taq DNA polymerase buffer with $MgCl_2$ (Boehringer Mannheim, Indianapolis, Ind.), and $H_2O$ to 50 µL. Amplification was done using a GeneAmp® 9600 thermal cycler (Perkin Elmer, Foster City, Calif.) with the following thermocycle program: 94° C. for 1 min; 30 cycles of 94° C. for 20 sec, 55° C. for 30 sec, and 72° C. for 30 sec; 72° C. for 6 min; 4° C.

The dsDNA products of the PCR process were then subjected to asymmetric PCR using only a 3' primer to generate substantially only the anti-sense strand of the target genes. A 100 µL reaction was done for each dsDNA product with 200 µmol of 3' primer, 2 µL of ds-DNA product, 0.5 µL Taq DNA Polymerase, 10 µL 2 mM dNTP's, 10 µL 10× Taq DNA polymerase buffer with $MgCl_2$ (Boehringer Mannheim, Indianapolis, Ind.), and $H_2O$ to 100 µL. The same PCR program as that described above was used to amplify the single-stranded (ss)-DNA.

Purification of Single-Stranded DNA by High Performance Liquid Chromatography and Kinasing Single-Stranded DNA The H chain ss-PCR products and the L chain single-stranded PCR products were ethanol precipitated by adding 2.5 volumes ethanol and 0.2 volumes 7.5 M ammonium acetate and incubating at −20° C. for at least 30 min. The DNA was pelleted by centrifuging in an Eppendorf centrifuge at 14 krpm for 10 min at 2-8° C. The supernatant was carefully aspirated, and the tubes were briefly spun a 2nd time. The last drop of supernatant was removed with a pipette. The DNA was dried in vacuo for 10 min on medium heat. The H chain products were pooled in 210 µL water and the L chain products were pooled separately in 210 µL water. The single-stranded DNA was purified by high performance liquid chromatography (HPLC) using a Hewlett Packard 1090 HPLC and a Gen-Pak™ FAX anion exchange column (Millipore Corp., Milford, Mass.). The gradient used to purify the single-stranded DNA is shown in Table 1, and the oven temperature was 60° C. Absorbance was monitored at 260 nm. The single-stranded DNA eluted from the HPLC was collected in 0.5 min fractions. Fractions containing single-stranded DNA were ethanol precipitated, pelleted and dried as described above.

The dried DNA pellets were pooled in 200 µL sterile water.

TABLE 1

HPLC gradient for purification of ss-DNA

| Time (min) | % A | % B | % C | Flow (ml/min) |
|---|---|---|---|---|
| 0 | 70 | 30 | 0 | 0.75 |
| 2 | 40 | 60 | 0 | 0.75 |
| 17 | 15 | 85 | 0 | 0.75 |
| 18 | 0 | 100 | 0 | 0.75 |
| 23 | 0 | 100 | 0 | 0.75 |
| 24 | 0 | 0 | 100 | 0.75 |
| 28 | 0 | 0 | 100 | 0.75 |
| 29 | 0 | 100 | 0 | 0.75 |
| 34 | 0 | 100 | 0 | 0.75 |
| 35 | 70 | 30 | 0 | 0.75 |

Buffer A is 25 mM Tris, 1 mM EDTA, pH 8.0
Buffer B is 25 mM Tris, 1 mM EDTA, 1 M NaCl, pH 8.0
Buffer C is 40 mm phosphoric acid The single-stranded DNA was 5'-phosphorylated in preparation for mutagenesis. Twenty-four µL 10× kinase buffer (United States Biochemical, Cleveland, Ohio), 10.4 µL 10 mM adenosine-5'-triphosphate (Boehringer Mannheim, Indianapolis, Ind.), and 2 µL polynucleotide kinase (30 units/µL, United States Biochemical, Cleveland, Ohio) was added to each sample, and the tubes were incubated at 37° C. for 1 hr. The reactions were stopped by incubating the tubes at 70° C. for 10 min. The DNA was purified with one extraction of Tris equilibrated phenol (pH>8.0, United States Biochemical, Cleveland, Ohio):chloroform:isoamyl alcohol (50:49:1) and one extraction with chloroform:isoamyl:alcohol (49:1). After the extractions, the DNA was ethanol precipitated and pelleted as described above. The DNA pellets were dried, then dissolved in 50 µL sterile water. The concentration was determined by measuring the absorbance of an aliquot of the DNA at 260 nm using 33 µg/ml for an absorbance of 1.0. Samples were stored at −20° C.

Preparation of Uracil Templates Used in Generation of Spleen Antibody Phage Libraries One ml of *E. coli* CJ236 (BioRAD, Hercules, Calif.) overnight culture was added to 50 ml 2xYT in a 250 ml baffled shake flask. The culture was grown at 37° C. to $OD_{600}$=0.6, inoculated with 10 µl of a 1/100 dilution of BS45 vector phage stock (described in U.S. patent application Ser. No. 08/835,159, filed Apr. 4, 1997) and growth continued for 6 hr. Approximately 40 ml of the culture was centrifuged at 12 krpm for 15 minutes at 4° C. The supernatant (30 ml) was transferred to a fresh centrifuge tube and incubated at room temperature for 15 minutes after the addition of 15 µl of 10 mg/ml RNaseA (Boehringer Mannheim, Indianapolis, Ind.). The phage were precipitated by the addition of 7.5 ml of 20% polyethylene glycol 8000 (Fisher Scientific, Pittsburgh, Pa.)/3.5M ammonium acetate (Sigma Chemical Co., St. Louis, Mo.) and incubation on ice for 30 min. The sample was centrifuged at 12 krpm for 15 min at 2-8° C. The supernatant was carefully discarded, and the tube briefly spun to remove all traces of supernatant. The pellet was resuspended in 400 µl of high salt buffer (300 mM NaCl, 100 mM Tris pH 8.0, 1 mM EDTA), and transferred to a 1.5 ml tube.

The phage stock was extracted repeatedly with an equal volume of equilibrated phenol:chloroform:isoamyl alcohol (50:49:1) until no trace of a white interface was visible, and then extracted with an equal volume of chloroform:isoamyl alcohol (49:1). The DNA was precipitated with 2.5 volumes of ethanol and 1/5 volume 7.5 M ammonium acetate and incubated 30 min at −20° C. The DNA was centrifuged at 14 krpm for 10 min at 4° C., the pellet washed once with cold 70% ethanol, and dried in vacuo. The uracil template DNA was dissolved in 30 µl sterile water and the concentration determined by $A_{260}$ using an absorbance of 1.0 for a concentration of 40 µg/ml. The template was diluted to 250 ng/µL with sterile water, aliquoted, and stored at −20° C.

Mutagenesis of Uracil Template with SS-DNA and Electroporation into *E. coli* to Generate Antibody Phage Libraries Antibody phage display libraries were generated by simultaneously introducing single-stranded heavy and light chain genes onto a phage display vector uracil template. A typical mutagenesis was performed on a 2 µg scale by mixing the following in a 0.2 ml PCR reaction tube: 8 µl of (250 ng/µL) uracil template, 8 µL of 10× annealing buffer (200 mM Tris pH 7.0, 20 mM $MgCl_2$, 500 mM NaCl), 3.33 µl of kinased single-stranded heavy chain insert (100 ng/µL), 3.1 µl of kinased single-stranded light chain insert (100 ng/µL), and sterile water to 80 µl. DNA was annealed in a GeneAmp® 9600 thermal cycler using the following thermal profile: 20 sec at 94° C., 85° C. for 60 sec, 85° C. to 55° C. ramp over 30 min, hold at 55° C. for 15 min. The DNA was transferred to ice after the program finished. The extension/ligation was carried out by adding 8 µl of 10× synthesis buffer (5 mM each dNTP, 10 mM ATP, 100 mM Tris pH 7.4, 50 mM $MgCl_2$, 20 mM DTT), 8 µL T4 DNA ligase (1 U/µL, Boehringer Mannheim, Indianapolis, Ind.), 8 µL diluted T7 DNA polymerase (1 U/µL, New England BioLabs, Beverly, Mass.) and incubating at 37° C. for 30 min. The reaction was stopped with 300 µL of mutagenesis stop buffer (10 mM Tris pH 8.0, 10 mM EDTA). The mutagenesis DNA was extracted once with equilibrated phenol (pH>8):chloroform:isoamyl alcohol (50:49:1), once with chloroform:isoamyl alcohol (49:1), and the DNA was ethanol precipitated at −20° C. for at least 30 min. The DNA was pelleted and the supernatant carefully removed as described above. The sample was briefly spun again and all traces of ethanol removed with a pipetman. The pellet was dried in vacuo. The DNA was resuspended in 4 µL of sterile water.

One microliter of mutagenesis DNA (500 ng) was transferred into 40 µl electrocompetent *E. coli* DH12S (Gibco/BRL, Gaithersburg, Md.) using electroporation. The transformed cells were mixed with approximately 1.0 ml of overnight XL-1 cells which were diluted with 2xYT broth to 60% the original volume. This mixture was then transferred to a 15-ml sterile culture tube and 9 ml of top agar added for plating on a 150-mm LB agar plate. Plates were incubated for 4 hrs at 37° C. and then transferred to 20° C. overnight. First round antibody phage were made by eluting phage off these plates in 10 ml of 2xYT, spinning out debris, and taking the supernatant. These samples are the antibody phage display libraries used for selecting antibodies against SAP. Efficiency of the electroporations was measured by plating 10 µl of a $10^{-4}$ dilution of suspended cells on LB agar plates, follow by overnight incubation of plates at 37° C. The efficiency was calculated by multiplying the number of plaques on the $10^{-4}$ dilution plate by $10^6$. Library electroporation efficiencies are typically greater than $1 \times 10^7$ phage under these conditions.

Transformation of *E. Coli* by Electroporation

Electrocompetent *E. coli* cells were thawed on ice. DNA was mixed with 40 L of these cells by gently pipetting the cells up and down 2-3 times, being careful not to introduce an air bubble. The cells were transferred to a Gene Pulser cuvette (0.2 cm gap, BioRAD, Hercules, Calif.) that had been cooled on ice, again being careful not to introduce an air bubble in the transfer. The cuvette was placed in the *E. coli* Pulser (BioRAD, Hercules, Calif.) and electroporated with the voltage set at 1.88 kV according to the manufacturer's recommendation. The transformed sample was immediately resuspended in 1 ml of 2xYT broth or 1 ml of a mixture of 400 µl 2xYT/600 µl overnight XL-1 cells and processed as procedures dictated.

Plating M13 Phage or Cells Transformed with Antibody Phage-Display Vector Mutagenesis Reaction Phage samples were added to 200 µL of an overnight culture of *E. coli* XL1-Blue when plating on 100 mm LB agar plates or to 600 µL of overnight cells when plating on 150 mm plates in sterile 15 ml culture tubes. After adding LB top agar (3 ml for 100 mm plates or 9 ml for 150 mm plates, top agar stored at 55° C. (see, Appendix A1, Sambrook et al., supra.), the mixture was evenly distributed on an LB agar plate that had been pre-warmed (37° C.-55° C.) to remove any excess moisture on the agar surface. The plates were cooled at room temperature until the top agar solidified. The plates were inverted and incubated at 37° C. as indicated.

Preparation of Biotinylated Sap and Biotinylated Antibodies

Concentrated recombinant SAP antigen (Example 2 above) was extensively dialyzed into BBS (20 mM borate, 150 mM NaCl, 0.1% NaN$_3$, pH 8.0). After dialysis, 1 mg of SAP (1 mg/ml in BBS) was reacted with a 15 fold molar excess of biotin-XX-NHS ester (Molecular Probes, Eugene, Oreg., stock solution at 40 mM in DMSO). The reaction was incubated at room temperature for 90 min and then quenched with taurine (Sigma Chemical Co., St. Louis, Mo.) at a final concentration of 20 mM. The biotinylated reaction mixture was then dialyzed against BBS at 2-8° C. After dialysis, biotinylated SAP was diluted in panning buffer (40 mM Tris, 150 mM NaCl, 20 mg/ml BSA, 0.1% Tween 20, pH 7.5), aliquoted, and stored at −80° C. until needed.

Antibodies were reacted with 3-(N-maleimidylpropionyl) biocytin (Molecular Probes, Eugene, Oreg.) using a free cysteine located at the carboxy terminus of the heavy chain. Antibodies were reduced by adding DTT to a final concentration of 1 mM for 30 min at room temperature. Reduced antibody was passed through a Sephadex G50 desalting column equilibrated in 50 mM potassium phosphate, 10 mM boric acid, 150 mM NaCl, pH 7.0. 3-(N-maleimidylpropionyl)-biocytin was added to a final concentration of 1 mM and the reaction allowed to proceed at room temperature for 60 min. Samples were then dialyzed extensively against BBS and stored at 2-8° C.

Preparation of Avidin Magnetic Latex

The magnetic latex (Estapor, 10% solids, Bangs Laboratories, Fishers, Ind.) was thoroughly resuspended and 2 ml aliquoted into a 15 ml conical tube. The magnetic latex was suspended in 12 ml distilled water and separated from the solution for 10 min using a magnet (PerSeptive Biosystems, Framingham, Mass.). While maintaining the separation of the magnetic latex with the magnet, the liquid was carefully removed using a 10 ml sterile pipette. This washing process was repeated an additional three times. After the final wash, the latex was resuspended in 2 ml of distilled water. In a separate 50 ml conical tube, 10 mg of avidin-HS (NeutrAvidin, Pierce, Rockford, Ill.) was dissolved in 18 ml of 40 mM Tris, 0.15 M sodium chloride, pH 7.5 (TBS). While vortexing, the 2 ml of washed magnetic latex was added to the diluted avidin-HS and the mixture mixed an additional 30 seconds. This mixture was incubated at 45° C. for 2 hr, shaking every 30 minutes. The avidin magnetic latex was separated from the solution using a magnet and washed three times with 20 ml BBS as described above. After the final wash, the latex was resuspended in 10 ml BBS and stored at 4° C.

Immediately prior to use, the avidin magnetic latex was equilibrated in panning buffer (40 mM Tris, 150 mM NaCl, 20 mg/ml BSA, 0.1% Tween 20, pH 7.5). The avidin magnetic latex needed for a panning experiment (200 µl/sample) was added to a sterile 15 ml centrifuge tube and brought to 10 ml with panning buffer. The tube was placed on the magnet for 10 min to separate the latex. The solution was carefully removed with a 10 ml sterile pipette as described above. The magnetic latex was resuspended in 10 ml of panning buffer to begin the second wash. The magnetic latex was washed a total of 3 times with panning buffer. After the final wash, the latex was resuspended in panning buffer to the starting volume.

Example 4

Selection of Recombinant Polyclonal Antibodies to
*Bacillus anthracis* SAP Antigen Binding reagents that specifically bind to *B. anthracis* SAP were selected from the phage display libraries created from hyperimmunized mice as described in Example 3.

Panning

First round antibody phage were prepared as described in Example 3 using BS45 uracil template. Electroporations of mutagenesis DNA were performed yielding phage samples derived from different immunized mice. To create more diversity in the recombinant polyclonal library, each phage sample was panned separately.

Before the first round of functional panning with biotinylated SAP antigen, antibody phage libraries were selected for phage displaying both heavy and light chains on their surface by panning with 7F11-magnetic latex (as described in Examples 21 and 22 of U.S. patent application Ser. No. 08/835,159, filed Apr. 4, 1997). Functional panning of these enriched libraries was performed in principle as described in Example 16 of U.S. patent application Ser. No. 08/835,159. Specifically, 10 µL of 1×10$^{-6}$ M biotinylated SAP antigen was added to the phage samples (approximately 1×10$^{-8}$ M SAP final concentration), and the mixture allowed to come to equilibrium overnight at 2-8° C.

After reaching equilibrium, samples were panned with avidin magnetic latex to capture antibody phage bound to SAP. Equilibrated avidin magnetic latex (Example 3), 200 µL latex per sample, was incubated with the phage for 10 min at room temperature. After 10 min, approximately 9 ml of panning buffer was added to each phage sample, and the magnetic latex separated from the solution using a magnet. After a ten minute separation, unbound phage was carefully removed using a 10 ml sterile pipette. The magnetic latex was then resuspended in 10 ml of panning buffer to begin the second wash. The latex was washed a total of three times as described above. For each wash, the tubes were in contact with the magnet for 10 min to separate unbound phage from the magnetic latex. After the third wash, the magnetic latex was resuspended in 1 ml of panning buffer and transferred to a 1.5 mL tube. The entire volume of magnetic latex for each sample was then collected and resuspended in 200 ul 2xYT and plated on 150 mm LB plates as described in Example 3 to amplify bound phage. Plates were incubated at 37° C. for 4 hr, then overnight at 20° C.

The 150 mm plates used to amplify bound phage were used to generate the next round of antibody phage. After the overnight incubation, second round antibody phage were eluted from the 150 mm plates by pipetting 10 mL of 2xYT media onto the lawn and gently shaking the plate at room temperature for 20 min. The phage samples were then transferred to 15 ml disposable sterile centrifuge tubes with a plug seal cap, and the debris from the LB plate pelleted by centrifuging the tubes for 15 min at 3500 rpm. The supernatant containing the second round antibody phage was then transferred to a new tube.

A second round of functional panning was set up by diluting 100 μL of each phage stock into 900 μL of panning buffer in 15 ml disposable sterile centrifuge tubes. Biotinylated SAP antigen was then added to each sample as described for the first round of panning, and the phage samples incubated for 1 hr at room temperature. The phage samples were then panned with avidin magnetic latex as described above. The progress of panning was monitored at this point by plating aliquots of each latex sample on 100 mm LB agar plates to determine the percentage of kappa positives. The majority of latex from each panning (99%) was plated on 150 mm LB agar plates to amplify the phage bound to the latex. The 100 mm LB agar plates were incubated at 37° C. for 6-7 hr, after which the plates were transferred to room temperature and nitrocellulose filters (pore size 0.45 mm, BA85 Protran, Schleicher and Schuell, Keene, N.H.) were overlaid onto the plaques.

Plates with nitrocellulose filters were incubated overnight at room temperature and then developed with a goat anti-mouse kappa alkaline phosphatase conjugate to determine the percentage of kappa positives as described below. Phage samples with lower percentages (<70%) of kappa positives in the population were subjected to a round of panning with 7F11-magnetic latex before performing a third functional round of panning overnight at 2-8° C. using biotinylated SAP antigen at approximately $2\times10^{-9}$ M. This round of panning was also monitored for kappa positives. Individual phage samples that had kappa positive percentages greater than 80% were pooled and subjected to a final round of panning overnight at 2-8° C. at $5\times10^{-9}$ M SAP. Antibody genes contained within the eluted phage from this fourth round of functional panning were subcloned into the expression vector, pBRncoH3.

The subcloning process was done generally as described in Example 18 of U.S. patent application Ser. No. 08/835,159. After subcloning, the expression vector was electroporated into DH10B cells and the mixture grown overnight in 2xYT containing 1% glycerol and 10 μg/ml tetracycline. After a second round of growth and selection in tetracycline, aliquots of cells were frozen at −80° C. as the source for SAP polyclonal antibody production. Two polyclonal antibodies, designated IIT004.1 and IIT005.1, were selected from two libraries derived from different sets of spleens. Monoclonal antibodies were selected from these polyclonal mixtures by plating a sample of the mixture on LB agar plates containing 10 μg/ml tetracycline and screening for antibodies that recognized SAP.

Detection of Alkaline Phosphatase Conjugates

After overnight incubation of nitrocellulose filters on LB agar plates, filters were carefully removed from the plates with membrane forceps and incubated for 2 hr in 10 mM TRIS, 150 mM NaCl, 10 mM $MgCl_2$, 0.1 mM $ZnCl_2$, 0.1% polyvinyl alcohol, 1% bovine serum albumin, 0.1% sodium azide, pH 8.0 (Block buffer). After 2 hr, the filters were incubated with goat anti-mouse kappa-AP (Southern Biotechnology Associates, Inc, Birmingham, Ala.) for 2-4 hours. The goat anti-mouse kappa-AP was diluted into Block buffer at a final concentration of 1 μg/ml. Filters were washed three times with 40 mM Tris, 150 mM NaCl, 0.05% Tween 20, pH 7.5 (TBST) for 5 min each. After the final wash, the filters were developed in a solution containing 0.2 M 2-amino-2-methyl-1-propanol (JBL Scientific, San Luis Obispo, Calif.), 0.5 M Tris, 0.33 mg/ml nitro blue tetrazolium ((NBT) Fisher Scientific, Pittsburgh, Pa.) and 0.166 mg/ml 5-bromo-4-chloro-3-indolyl-phosphate, p-toluidine salt.

Expression and Purification of Recombinant Antibodies Against SAP

A shake flask inoculum was generated overnight from a −70° C. cell bank in an Innova 4330 incubator shaker (New Brunswick Scientific, Edison, N.J.) set at 37° C., 300 rpm. The inoculum was used to seed a 20 L fermentor (Applikon, Foster City, Calif.) containing defined culture medium (Pack et al. (1993) *Bio/Technology* 11: 1271-1277) supplemented with 3 g/L L-leucine, 3 g/L L-isoleucine, 12 g/L casein digest (Difco, Detroit, Mich.), 12.5 g/L glycerol and 10 μg/ml tetracycline. The temperature, pH and dissolved oxygen in the fermentor were controlled at 26° C., 6.0-6.8 and 25% saturation, respectively. Foam was controlled by addition of polypropylene glycol (Dow, Midland, Mich.). Glycerol was added to the fermentor in a fed-batch mode. Fab expression was induced by addition of L(+)-arabinose (Sigma, St. Louis, Mo.) to 2 g/L during the late logarithmic growth phase. Cell density was measured by optical density at 600 nm in an UV-1201 spectrophotometer (Shimadzu, Columbia, Md.). Following run termination and adjustment of pH to 6.0, the culture was passed twice through an M-210B-EH Microfluidizer (Microfluidics, Newton, Mass.) at 17,000 psi. The high pressure homogenization of the cells released the Fab into the culture supernatant.

The first step in purification was expanded bed immobilized metal affinity chromatography (EB-IMAC). Streamline™ chelating resin (Pharmacia, Piscataway, N.J.) was charged with 0.1 M $NiCl_2$ and was then expanded and equilibrated in 50 mM acetate, 200 mM NaCl, 10 mM imidazole, 0.01% $NaN_3$, pH 6.0 buffer flowing in the upward direction. A stock solution was used to bring the culture homogenate to 10 mM imidazole, following which it was diluted two-fold or higher in equilibration buffer to reduce the wet solids content to less than 5% by weight. It was then loaded onto the Streamline column flowing in the upward direction at a superficial velocity of 300 cm/hr. The cell debris passed through unhindered, but the Fab was captured by means of the high affinity interaction between nickel and the hexahistidine tag on the Fab heavy chain. After washing, the expanded bed was converted to a packed bed and the Fab was eluted with 20 mM borate, 150 mM NaCl, 200 mM imidazole, 0.01% $NaN_3$, pH 8.0 buffer flowing in the downward direction.

The second step in the purification used ion-exchange chromatography (IEC). Q Sepharose FastFlow resin (Pharmacia, Piscataway, N.J.) was equilibrated in 20 mM borate, 37.5 mM NaCl, 0.01% $NaN_3$, pH 8.0. The Fab elution pool from the EB-IMAC step was diluted four-fold in 20 mM borate, 0.01% $NaN_3$, pH 8.0 and loaded onto the IEC column. After washing, the Fab was eluted with a 37.5-200 mM NaCl salt gradient. The elution fractions were evaluated for purity using an Xcell II™ SDS-PAGE system (Novex, San Diego, Calif.) prior to pooling. Finally, the Fab pool was concentrated and diafiltered into 20 mM borate, 150 mM NaCl, 0.01% $NaN_3$, pH 8.0 buffer for storage. This was achieved in a Sartocon Slice™ system fitted with a 10,000 MWCO cassette (Sartorius, Bohemia, N.Y.). The final purification yields were typically 50%. The concentration of the purified Fab was measured by UV absorbance at 280 nm, assuming an absorbance of 1.6 for a 1 mg/ml solution.

Culture of *Bacillus* Spp. and Preparation of Cleared Culture Supernatant Antigen Nonencapsulated *Bacillus anthracis*, Sterne strain was obtained from the Colorado Serum Company. *B. cereus* OH599 was the kind gift of Dr. A. Kotiranta, *B. globigii* was obtained from Dr. L. Larson, and *B. thuringiensis* 10792 was obtained from the American Type Culture Collection (Manassas, Va.). Organisms were cultured on tryptic soy agar containing 5% sheep blood (Hardy Diagnostics, Santa Maria, Calif.) or in brain heart infusion broth (Becton Dickinson and Company, Cockeysville, Md.) at 37° C.

For preparation of cleared culture supernatant antigens, *B. anthracis*, Sterne strain was grown in brain heart infusion broth at 37° C. with aeration for 24 h. A sample of the culture was serially diluted 10-fold in sterile 0.01M phosphate buffered saline, pH 7.4 (PBS) and 100 μl of each dilution was plated on a blood agar plate for determination of the number of viable organisms. The culture was subjected to centrifugation at 10,000×g for 20 min at 4° C. using a J2-21 centrifuge (Beckman, Fullerton, Calif.). The supernatant was transferred to a sterile bottle and a protease inhibitor cocktail (Sigma-Aldrich, Inc) was added. The sample was filtered using a 0.2 μm pore-size membrane filter unit (Millipore Corp., Bedford, Mass.) then dialyzed in 4 L of 0.01M PBS, pH 7.4, 2 mM EDTA, 0.1 mM phenymethylsulfonyl fluoride at 4° C. with four buffer changes in 24 h. The dialyzed sample was aliquoted and stored at −80° C. The concentration of SAP in the cleared culture supernatant was quantified by a sandwich enzyme-linked immunosorbant assay using purified recombinant SAP as a standard. Analysis of the amount of SAP recovered from the culture supernatant indicated that 1 ng of SAP corresponded to approximately $2.9\times10^3$ organisms (i.e. 0.35 pg/organism).

Example 5

Selection of Monoclonal Antibodies to SAP from the Recombinant Polyclonal Antibody Mixtures Monoclonal antibodies against SAP were isolated from clones containing the recombinant polyclonal mixtures (Example 4) by plating a diluted sample of the mixture on LB agar plates containing 10 μg/ml tetracycline. Individual colonies were then tested for the ability to produce antibody that recognized recombinant SAP using surface plasmon resonance (BIACORE)(BIACORE, Uppsala, Sweden). Small scale production of these monoclonal antibodies was accomplished using a Ni-chelate batch-binding method (see below). Antibodies isolated from this method were diluted 1:3 in HBS-EP (0.01 M HEPES, pH 7.4, 0.15 M NaCl, 3 mM EDTA, 0.005% polysorbate 20 (v/v)), captured with a goat anti-mouse kappa antibody (Southern Biotechnology Associates, Inc, Birmingham, Ala.) coupled to a BIACORE CM5 sensor chip, and tested for the ability to bind recombinant SAP. Antibodies that bound SAP were then evaluated using BIACORE epitope mapping analysis. Antibodies that bound distinct epitopes were produced on a larger scale and then conjugated to biotin and alkaline phosphatase. These conjugates were then tested in an ELISA assay to determine the sensitivity and utility of these antibodies.

Minipreparation of Monoclonal Antibodies by Ni-Chelate Batch-Binding Method

Individual colonies were isolated from the recombinant polyclonal mixtures (Example 4) and used to inoculate 3 ml cultures of 2xYT medium containing 1% glycerol supplemented with 10 μg/ml tetracycline. These cultures were grown in an Innova 4330 incubator shaker (New Brunswick Scientific, Edison, N.J.) set at 37° C., 300 rpm. The next morning 0.5 ml of each culture was used to inoculate shake flasks containing 50 ml of defined medium, (Pack et al. (1993) *Bio/Technology* 11: 1271-1277) supplemented with 3 g/L L-leucine, 3 g/L L-isoleucine, 12 g/L casein digest (Difco, Detroit, Mich.), 12.5 g/L glycerol and 10 μg/ml tetracycline. These cultures were shaken at 300 rpm, 37° C. until an optical density of 4 was reached at 600 nm. Fab expression was then induced by adding L(+)-arabinose (Sigma, St. Louis, Mo.) to 2 g/L and shifting the temperature to 23° C. with overnight shaking. The next day the following was added to the 50 ml cultures: 0.55 ml of 1 M imidazole, 5 ml B-PER (Pierce, Rockford, Ill.) and 2 ml Ni-chelating resin (Chelating Sepharose FastFlow™ resin Pharmacia, Piscataway, N.J.). The mixture was shaken at 300 rpm, 23° C. for 1 hour after which time shaking was stopped and the resin allowed to settle to the bottom of the flasks for 15 minutes.

The supernatant was then poured off and the resin resuspended in 40 ml of BBS (20 mM borate, 150 mM NaCl, 0.1% $NaN_3$, pH 8.0) containing 10 mM imidazole. This suspension was transferred to a 50 ml conical tube and the resin washed a total of 3 times with BBS containing 10 mM imidazole. Washing was accomplished by low speed centrifugation (1100 rpm for 1 minute), removal of supernatant and, resuspension of the resin in BBS containing 10 mM imidazole. After the supernatant of the final wash was poured off, 0.5 ml of 1 M imidazole was added to each tube, vortex briefly, and transferred to a sterile microcentrifuge tube. The samples were then centrifuged at 14 krpm for 1 minutes and the supernatant transferred to a new microcentrifuge tube. Antibodies contained in the supernatant were then analyzed for binding to SAP using a BIACORE (BIACORE, Uppsala, Sweden).

Selection and Cloning of a Recombinant Polyclonal Antibody Complementary to IIT005.1.13 and IIT005.1.C.11 Monoclonal Antibodies A monoclonal antibody designated IIT004.1.12 was selected from the polyclonal library designated IIT004.1, biotinylated, and 15 μl of a $10^{-6}$ M solution was mixed with soluble recombinant SAP antigen (7.5 μl of a $10^{-7}$ M solution). This mixture was incubated for 15 minutes at room temperature. Fifteen microliters of each mixture was added to 50 μl of phage library IIT005.1 diluted in 1 ml panning buffer (40 mM Tris, 150 mM NaCl, 20 mg/ml BSA, 0.1% Tween 20, pH 7.5) and incubated overnight at 2-8° C. Final concentrations were $10^{-8}$ M biotinylated monoconal antibody and $5\times10^{-10}$ M SAP. The sample was panned with avidin magnetic latex and plated as described in Example 4. The eluted phage were subjected to another round of selection using these conditions and the resulting polyclonal library was designated IIT005.1.C. Two monoclonal antibodies designated IIT005.1.13 and IIT005.1.C.11 were selected from the IIT005.1 and IIT005.1.C libraries respectively, biotinylated and complexed with SAP using the conditions described above. Complementary polyclonal antibodies were selected as described above from phage library IIT005.1 using monoclonal antibodies IIT005.1.13 and IIT005.1.C.11. These complementary polyclonal antibodies were designated IIT005.1.13.1 and IIT005.1.C.11.1 and were subcloned as described in Example 18 of U.S. patent application Ser. No. 08/835,159.

Example 6

Specificity of Monoclonal/Polyclonal Antibodies to SAP Determined by Western Blot and Indirect Immunofluorescence Analysis The specificity of monoclonal and polyclonal antibodies against *B. anthracis*, Sterne strain SAP was visualized by Western blot analysis. Recombinant antibodies against SAP were tested for reactivity to recombinant SAP as well as to SAP isolated from the cleared culture supernatant of *Bacillus anthracis* Sterne strain. Cross reactivity to other *Bacillus* strains was also tested. Culture supernatant proteins and whole cell lysates of *B. anthracis*, Sterne strain, *B. cereus* OH599, *B. globigii* and *B. thuringiensis* 10792 equivalent to $10^8$ organisms were separated by electrophoresis in 4-20% TRIS-glycine SDS-polyacrylamide gels (Novex, San Diego, Calif.) under reducing conditions. The proteins were transferred to ProBlott™ membranes (Applied Biosystems, Foster City, Calif.) using 10 mM CAPS/10% methanol transfer buffer. The membranes were blocked in 10 mM TRIS, 150 mM NaCl, 10 mM $MgCl_2$, 0.1 mM $ZnCl_2$, 0.1% polyvinyl alcohol, 1% bovine serum albumin, 0.1% sodium azide, pH 8.0 (Block buffer) for 1 h at room temperature.

The membranes were then incubated in 5 μg/ml of monoclonal or recombinant polyclonal antibody diluted in Block buffer for 1 h and then washed three times with 40 mM TRIS, 150 mM NaCl, 0.05% Tween 20, pH 7.5 (TBST) (Fisher Chemical, Pittsburgh, Pa.) for 5 min each. After washing, the membranes were incubated in rabbit anti-mouse IgG (H&L)-alkaline phosphatase conjugate (Southern Biotechnology, Inc, Birmingham, Ala.) diluted 1:1000 in Block buffer. The membranes were washed three times with TBST for 5 min each and developed in a solution containing 0.2 M 2-amino-2-methyl-1-propanol (JBL Scientific, San Luis Obispo, Calif.), 0.5 M TRIS, 0.33 mg/ml nitro blue tetrazolium ((NBT) Fisher Scientific, Pittsburgh, Pa.) and 0.166 mg/ml 5-bromo-4-chloro-3-indolyl-phosphate, p-toluidine salt.

The anti-SAP recombinant polyclonal antibodies reacted with recombinant SAP, SAP protein isolated from the culture supernatant, and the cell pellet of *B. anthracis*, Sterne strain. The antibodies did not react with any proteins in the culture supernatant or cell pellet of the other *Bacillus* species tested (*B. cereus* and *thuringiensis*). A goat anti-anthrax polyclonal serum was used to demonstrate cross-reactivity of *B. anthracis* antibodies with proteins of other *Bacillus* species (data not shown). Conjugates alone served as negative controls.

The specificity of antibodies against *B. anthracis*, Sterne strain was also tested by indirect immunofluorescence. Localization of SAP to the outer membrane of unencapsulated *B. anthracis*, Sterne strain was demonstrated using an indirect immunofluorescence technique. *B. anthracis*, *B. cereus*, and *B. thuringiensis* were washed and resuspended in PBS to yield $1 \times 10^8$ organisms per ml. Four microliters of the suspensions were applied to wells of an eight well microscope slide and allowed to air dry. The slides were lightly heated to fix the smears to the slide and covered with 0.1 mg/ml of antibody diluted in PBS containing 1% BSA. The smears were incubated with antibody for 1 h at 37° C. in a moist chamber. After washing the slides three times by soaking in PBS for 5 min each, the smears were covered with fluorescein isothiocyanate-conjugated rabbit anti-mouse IgG (H&L) F(ab')$_2$ (Zymed Laboratories, Inc., South San Francisco, Calif.) diluted 1:80 in PBS, 1% BSA, 0.05% Evans Blue (Sigma). The slides were incubated for 1 h at 37C in a moist chamber then washed as described above. After a final wash in deionized water, the slides were allowed to air dry in the dark. Coverslips were mounted using a 90% glycerol mounting medium containing 10 mg/ml p-phenylenediamine, pH 8.0.

The slides were examined for fluorescent organisms using an epifluorescence microscope with a 63× objective lens (Leitz Wetzler Germany). The recombinant polyclonal antibody (ITT005.1) demonstrated 4+ fluorescence with unencapsulated *B. anthracis* and did not react with *B. cereus*, or *B. thuringiensis*. Negative controls included fluorescein-conjugated antibody alone, and a murine polyclonal antiserum specific for *B. anthracis*, Sterne strain spore coat proteins.

Example 7

Sensitivity and Specificity of an ELISA Plate Assay for Detection of *B. anthracis* SAP This Example demonstrates that an ELISA assay using the reagents and methods of the invention are not only highly sensitive for *B. anthracis*, but are also highly specific for this particular *Bacillus* species.

The sensitivity and specificity of various monoclonal/recombinant polyclonal antibody pairs were determined by performing a sandwich assay using biotinylated monoclonal antibodies and alkaline phosphatase-conjugated recombinant polyclonal antibodies. Assays were performed with NeutraAvidin or streptavidin coated plates, such as Reacti-Bind™ streptavidin coated polystyrene 96 well plates (Pierce Chemical, Rockford, Ill.). After washing the 96 well plate with BBS (20 mM borate, 150 mM NaCl, 0.01% $NaN_3$, pH 8.0) containing 0.02% TWEEN-20, biotinylated monoclonal antibodies (50 μL of 2.5 μg/mL diluted in Block buffer (10 mM Tris, 150 mM NaCl, 10 mM $MgCl_2$, 0.1 mM $ZnCl_2$, 0.1% polyvinyl alcohol, 1% bovine serum albumin, 0.1% sodium azide, pH 8.0)) were added to the wells. The plate was incubated at room temperature for 1 hr.

The plate was then washed, after which various dilutions (10 ng/ml to 0.625 ng/ml) of soluble SAP antigen (50 μL of recombinant SAP or SAP in culture supernatants (as prepared in Example 4) were added in duplicate to the biotinylated monoclonal wells. The plates were incubated for one hour at room temperature or overnight at 2-8° C., after which the plate was washed. The appropriate recombinant polyclonal antibody-alkaline phosphatase conjugate (50 μL of 2.5 μg/mL diluted in Block) was added and incubated at room temperature for 1 hr. After 1 hr, the plate was washed and developed using the ELISA Amplification System (Gibco BRL, Gaithersburg, Md.) according to the manufacturer's instructions.

Results from several assays are compiled in accompanying tables 2-5. These data indicate that the assays can detect less than 0.625 ng of SAP protein. This amount of SAP corresponds to approximately $1.8 \times 10^3$ *Bacillus anthracis* organisms per ml. Significantly, little or no cross reactivity to other related *Bacillus* species was detected.

TABLE 2

| IIT005.1.C.11-BIOTIN WITH IIT005.1.C11.1-AP | | | | | |
|---|---|---|---|---|---|
| *B. anthracis* culture (cfu/ml) | A490 | SAP (ng/mL) | A490 | Undiluted *Bacillus* species | A490 |
| 28330 | 3.4 | 10 | 3.55 | cereus | 0.28 |
| 14165 | 2.8 | 5 | 3.45 | thuringiensis | 0.27 |
| 7083 | 2.14 | 2.5 | 2.94 | subtilis niger | 0.55 |
| 3541 | 1.56 | 1.25 | 2.01 | subtilis | 0.51 |
| 1770 | 1.17 | 0.625 | 1.51 | BHI broth | 0.48 |
| 0 | 0.92 | 0 | 0.92 | media | |

TABLE 3

IIT005.1.13-BIOTIN WITH IIT005.1.13.1-AP

| B. anthracis culture (cfu/ml) | A490 | Undiluted Bacillus species | A490 |
|---|---|---|---|
| 28330 | 3.13 | cereus | 0.28 |
| 14165 | 2.21 | thuringiensis | 0.27 |
| 7083 | 1.5 | subtilis niger | 0.48 |
| 3541 | 0.99 | subtilis | 0.5 |
| 1770 | 0.78 | BHI broth | 0.423 |
| 0 | 0.55 | media | |

TABLE 4

IIT005.1.C.11:BIOTIN WITH IIT005.1-AP

| B. anthracis culture (cfu/ml) | A490 | SAP (ng/mL) | A490 | Undiluted Bacillus species | A490 |
|---|---|---|---|---|---|
| 28330 | 2.87 | 10 | 3.4 | cereus | 0.09 |
| 14165 | 1.698 | 5 | 2.56 | thuringiensis | 0.14 |
| 7083 | 1 | 2.5 | 1.49 | subtilis niger | 0.13 |
| 3541 | 0.55 | 1.25 | 0.82 | subtilis | 0.14 |
| 1770 | 0.35 | 0.625 | 0.49 | BHI broth | 0.148 |
| 0 | 0.14 | 0 | 0.19 | media | |

TABLE 5

IIT005.1.13-BIOTIN WITH IIT005.1-AP

| B. anthracis culture (cfu/ml) | A490 | Undiluted Bacillus species | A490 |
|---|---|---|---|
| 28330 | 1.77 | cereus | 0.085 |
| 14165 | 0.99 | thuringiensis | 0.121 |
| 7083 | 0.54 | subtilis niger | 0.125 |
| 3541 | 0.34 | subtilis | 0.124 |
| 1770 | 0.23 | BHI broth | 0.125 |
| 0 | 0.14 | media | |

These results demonstrate that four different monoclonal/recombinant polyclonal antibody preparations exhibit great sensitivity for *B. anthracis* while not cross reacting with other *Bacillus* species.

Example 8

Assay for the Detection of Anthrax Infection in Humans

Blood samples from individuals suspected of exposure to *B. anthracis* are obtained by venous puncture and collected in tubes with (for plasma separation) or without (for serum separation) anti-coagulants present. Volumes of sample (100 µl) are contacted separately with either affinity agent for antibody detection or capture reagent for the detection of SAP antigen. These reagents are separately immobilized in different wells in a 96-well microtiter plate. The microtiter wells are coated so that they bind biotinylated molecules (REACTI-BIND™ NEUTRAVIDIN™, Pierce, Rockford, Ill.). Biotinylated SAP antigen and biotinylated capture antibody are added to their respective wells in volumes of 100 µl/well at concentrations of 2 µg/ml. After one hour of incubation at room temperature, the wells are washed with BBS to remove unbound reagent and the samples are added to each well. Negative control samples not containing SAP antigen or antibody to SAP antigen as well as positive control samples containing either SAP antigen or antibody to SAP antigen are added to separate wells prepared as described. The samples and controls are incubated with the immobilized reagents for one hour at room temperature, the samples are removed by aspiration and the wells are each washed using several one-ml volumes of BBS containing 0.05% TRITON X-100 detergent with aspiration between the addition of each volume of wash solution.

For the detection of human antibody in wells containing the biotinylated SAP antigen, alkaline phosphatase conjugates of mouse monoclonal antibodies specific for either human IgG (clone G18-145) or human IgM (clone G20-127, both from BD Biosciences/Pharmingen, San Diego, Calif.) are added in conjugate diluent at concentrations of 1 µg/ml and incubated for one hour at room temperature. For the detection of SAP antigen in samples one of the monoclonal antibodies described in Example 5 is biotinylated and used as the capture reagent and the other is conjugated to alkaline phosphatase and used as the detection reagent using the same assay steps as described for the detection of human antibodies. The wells are washed with BBS containing 0.05% TRITON X-100 as described. The amount of bound enzyme activity is detected by ELISA amplification reagents (Gibco BRL, Gaithersburg, Md.) according to the manufacturer's instructions. The absorbance at 490 nm is measured using a microtiter plate reader. From testing a population of clinical samples from healthy people a positive cutoff value is determined so that 95% of the normal samples values fall beneath the cutoff value. Any well or average of replicate wells that exceeds the cutoff value is considered a positive result. Higher specificities of 98% or 99% can be achieved by determining the appropriate cutoff value from the results with normal samples. The values measured in the positive control wells can be used to provide a rough calibration of the assay response so that the cutoff value can be determined as a percentage of the difference between the negative and positive control values. The presence of either human IgM or human IgG specific for SAP is determined as well as the presence of SAP antigen. The presence of any one of these in a human blood sample is indicative of infection with *B. anthracis*. The presence of either SAP antigen or specific IgM indicates that the patient has recently developed the infection. The presence of both specific IgM and IgG indicates an active infection that has progressed to a secondary immune response. The presence of specific IgG alone indicates that the patient was exposed, developed a secondary immune response and may have cleared the organism.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

What is claimed is:

1. A kit for the detection of an anti-*B. anthracis* antibody in a biological sample, the kit comprising an affinity agent non-diffusively immobilized on a solid support, the affinity agent comprising at least 10 contiguous amino acids of SEQ ID NO:1, wherein the affinity agent forms a first complex with the anti-*B. anthracis* antibody if the anti-*B. anthracis* antibody is contacted to the affinity agent.

2. The kit of claim 1, wherein the affinity agent comprises at least 10 contiguous amino acids of amino acids 180 to 700 of SEQ ID NO:1.

3. The kit of claim 1, wherein the affinity agent comprises SEQ ID NO:1.

4. The kit of claim 1, wherein the solid support comprises a microtiter plate and the affinity agent is present in the wells of the microtiter plate.

5. The kit of claim 1, further comprising a first detection reagent.

6. The kit of claim 5, wherein the first detection reagent comprises a detection antibody that binds to the first complex.

7. The kit of claim 6, wherein the detection antibody is labeled.

8. The kit of claim 7, where in the label is selected from the group consisting of enzymes, radioisotopes, fluorescent compounds, colloidal metals, chemiluminescent compounds, phosphorescent compounds and bioluminescent compounds.

9. The kit of claim 8, wherein the detection antibody specifically binds to a human antibody.

10. The kit of claim 9, wherein the human antibodies detected comprise IgG and IgM isotypes.

11. The kit of claim 1, further comprising a capture reagent immobilized on a solid support, wherein the capture reagent forms a second complex with a *B. anthracis* surface array protein if the surface array protein is present in the sample.

12. The kit of claim 11, wherein the capture reagent and affinity agent are immobilized on the same solid support.

13. The kit of claim 11, wherein the capture reagent is immobilized on a microtiter dish.

14. The kit of claim 11, wherein the capture reagent is a third antibody.

15. The kit of claim 14, wherein the capture reagent is a recombinant polyclonal antibody.

16. The kit of claim 14, wherein the capture reagent is a monoclonal antibody.

17. The kit of claim 11, wherein the kit further comprises a positive control that comprises a polypeptide that comprises an antigenic determinant of a *B. anthracis* surface array protein.

18. The kit of claim 17, herein the antigenic determinant comprises an amino acid sequence of SEQ ID NO:1.

19. The kit of claim 18, wherein the antigenic determinant comprises at least 10 contiguous amino acids of amino acids 180 to 700 of SEQ ID NO:1.

20. The kit of claim 11, further comprising a second detection reagent.

21. The kit of claim 20, wherein the second detection reagent comprises a fourth antibody that binds to the second complex.

22. The kit of claim 21, wherein the fourth antibody is labeled.

* * * * *